(12) United States Patent
Eckl et al.

(10) Patent No.: US 7,932,255 B2
(45) Date of Patent: Apr. 26, 2011

(54) 2-AMINOCARBONYL SUBSTITUTED PIPERAZINE OR DIAZA-CYCLIC COMPOUNDS AS APOPTOSIS PROTEIN INHIBITORS (LAP) MODULATORS

(75) Inventors: Robert Eckl, Munich (DE); Roswitha Taube, Graefelfing (DE); Michael Almstetter, Grasbrunn (DE); Michael Thormann, Martinsried (DE); Andreas Treml, Bodenmais (DE); Christopher Straub, Stow, MA (US); Zhouliang Chen, Belmont, MA (US)

(73) Assignee: Novartis AG, Basel (CH)

( * ) Notice: Subject to any disclaimer, the term of this patent is extended or adjusted under 35 U.S.C. 154(b) by 464 days.

(21) Appl. No.: 11/911,418

(22) PCT Filed: Apr. 13, 2006

(86) PCT No.: PCT/US2006/013943
§ 371 (c)(1),
(2), (4) Date: Oct. 12, 2007

(87) PCT Pub. No.: WO2006/113376
PCT Pub. Date: Oct. 26, 2006

(65) Prior Publication Data
US 2008/0207630 A1    Aug. 28, 2008

(51) Int. Cl.
*A61K 31/4965* (2006.01)
*A61K 31/00* (2006.01)
*C07D 241/04* (2006.01)
*C07D 295/00* (2006.01)
*C07D 243/08* (2006.01)
*A01N 43/00* (2006.01)

(52) U.S. Cl. .............. 514/255.01; 544/390; 540/575; 514/211.08

(58) Field of Classification Search ............... 544/390; 514/255.01, 211.08; 540/575
See application file for complete search history.

(56) References Cited

FOREIGN PATENT DOCUMENTS

| WO | WO 99/47545 A2 | | 9/1999 |
|---|---|---|---|
| WO | WO 02/080895 | * | 10/2002 |
| WO | WO 02/080895 A2 | | 10/2002 |
| WO | WO 2004/005248 A1 | | 1/2004 |

OTHER PUBLICATIONS

Rossen, et al., Asymmetric Hydrogenation of Tetrahydropyrazines: Synthesis of (S)-Piperazine-2-tert-butylcarboxamide, an Intermediate in the Preparation of the HIV Protease Inhibitor Indinavir, Tetrahedron Letters, vol. 36, No. 36, pp. 6419-6422 (1995).*

Kim, et al., Apicidin Potentiates the Imatinib-induced Apoptosis of Bcr-Abl-positive Human Leukaemia Cells by Enhancing the Activation of Mitochondria-dependent Caspase Cascades, British J. of Haematology, 124 166-178 (2004).*

Kipp, Rachael A. et al., "Molecular Targeting of Inhibitor of Apoptosis Bases on Small Molecule Mimics of Natural Binding Partners", Biochemistry, 41(23)7344-7349(2002), American Chemical Society, Easton, PA, US.

* cited by examiner

*Primary Examiner* — James O Wilson
*Assistant Examiner* — Erich A Leeser
(74) *Attorney, Agent, or Firm* — Novartis AG

(57) ABSTRACT

The present invention relates to compounds of formula (I) or pharmaceutically acceptable salts, solvates, hydrates or pharmaceutically acceptable formulations thereof. These compounds may be used to modulate cellular proliferation and to prevent and/or treat proliferative diseases.

10 Claims, No Drawings

2-AMINOCARBONYL SUBSTITUTED PIPERAZINE OR DIAZA-CYCLIC COMPOUNDS AS APOPTOSIS PROTEIN INHIBITORS (IAP) MODULATORS

This application is the National Stage of Application No. PCT/US2006/013943 filed on Apr. 13, 2006. The contents are incorporated herein by reference in their entirety.

The present invention relates to new compounds that modulate cellular proliferation and to prevent and/or treat proliferative diseases. Preferred compounds act to modulate the activity of an "inhibitor of apoptosis protein" (IAP). Most preferred compounds are inhibitors of IAP.

Programmed cell death (apoptosis) is a key mechanism for the development and maintenance of a multicellular organism. The organism only remains healthy if there is an equilibrium between new formation and elimination of cells. The consequence of this equilibrium being out of control is pathological manifestations such as cancer, hepatitis, Parkinson's disease, stroke, cardiac infarction etc.

Tumour cells may be distinguished from other cells in that, in particular, their reproduction is unchecked. They have devised various strategies of circumventing apoptosis. One molecular mechanism described only recently involves the overexpression of members of the IAP family that prevent apoptosis by direct interaction with and neutralisation of caspases.

Inhibiting substances for inhibitor of apoptosis protein (IAP) are therefore of great interest in the control of cancer. IAPs include, e.g., XIAP and CIAP.

It is the aim of the present invention to prepare a new type of compound that blocks (inhibits) IAP. Present compounds of the invention are alternatively referred to as Inhibitor of Apoptosis Protein inhibitors (IAPI).

The present invention relates to compounds of formula (I),

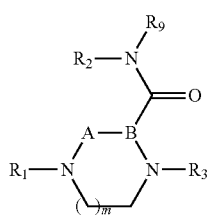

(I)

wherein $R^1$ is a hydrogen atom, or an alkyl, heteroalkyl, alkenyl, heteroalkenyl, alkynyl, heteroalkynyl, aryl, heteroaryl, cycloalkyl, heterocycloalkyl, alkylcycloalkyl, heteroalkylcycloalkyl, aralkyl or heteroaralkyl radical, any of which may be further substituted with at least one halogen;

$R^2$ is an alkyl, heteroalkyl, alkenyl, heteroalkenyl, alkynyl, heteroalkynyl, aryl, heteroaryl, cycloalkyl, heterocycloalkyl, alkylcycloalkyl, heteroalkylcycloalkyl, aralkyl or heteroaralkyl radical, any of which may be further substituted with at least one halogen;

$R^3$ is chosen from one of the following structures:

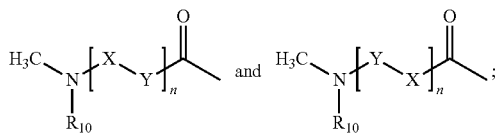

m is an integer 1, 2 or 3;
n is an integer 1, 2, 3, 4, 5 or 6;
A-B together are —CHR$^4$—CH—, —CR$^5$=C— or —CO—CH—;
each X, independently of one another, is a bond, an oxygen atom, a sulfur atom, a group of formula CR$^6$R$^7$, CO, NR$^8$, an optionally substituted cycloalkylene, an optionally substituted heterocycloalkylene, an optionally substituted arylene, or an optionally substituted heteroarylene group;
each Y, independently of one another, is a bond, an oxygen atom, a sulfur atom, a group of formula CR$^6$R$^7$, CO, NR$^8$, an optionally substituted cycloalkylene, an optionally substituted heterocycloalkylene, an optionally substituted arylene, or an optionally substituted heteroarylene group;
$R^4$ is a hydrogen atom, a halogen atom, or an alkyl, alkenyl, alkynyl, hetero-alkyl, aryl, heteroaryl, cycloalkyl, alkylcycloalkyl, heteroalkylcycloalkyl, heterocycloalkyl, aralkyl or heteroaralkyl radical;
$R^5$ is a hydrogen atom, or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;
the radicals $R^6$ independently of one another, are a hydrogen atom, or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;
the radicals $R^7$, independently of one another, are a hydrogen atom, or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;
the radicals $R^8$, independently of one another, are a hydrogen atom, or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;
$R^9$ is hydrogen or is an alkyl, heteroalkyl, aryl, heteroaryl, cycloalkyl, heterocycloalkyl, alkylcycloalkyl, heteroalkylcycloalkyl, aralkyl or hetero-aralkyl radical, or $R^2$ and $R^9$ with the nitrogen atom may form a heteroaryl or heteroaralkyl; and
$R^{10}$ is hydrogen or is an alkyl or heteroalkyl;
or a pharmacologically acceptable salt, solvate, hydrate or a pharmacologically acceptable formulation thereof.

Preferably, $R^1$ is, e.g., $SO_{(0-2)}R^4$; $COR^4$; $COOR^4$ or is $CONR^4R^5$.

As is evident to those skilled in the art, many of the compounds of the present invention contain asymmetric carbon atoms. It should be understood, therefore, that all individual stereoisomers of the provided formulas are contemplated as being included within the scope of this invention. Unless specifically stated, reference to any of the R groups in any of the provided formulations does not infer chirality or stereospecificity.

The expression alkyl refers to a saturated, straight-chained or branched hydrocarbon group, which has in particular 1 to 20 carbon atoms, preferably 1 to 12 carbon atoms, most preferably 1 to 6 carbon atoms, e.g. the methyl, ethyl, propyl, isopropyl, n-butyl, isobutyl, tert-butyl, n-hexyl, 2,2-dimethylbutyl or n-octyl group.

The expressions alkenyl and alkynyl refer to at least partly unsaturated, straight-chained or branched hydrocarbon groups that have in particular 2 to 20 carbon atoms, preferably 2 to 12 carbon atoms, most preferably 2 to 6 carbon atoms, e.g. the ethenyl, allyl, acetylenyl, propargyl, isoprenyl or hex-2-enyl group. Alkenyl groups preferably have one or two (most preferably one) double bond(s) and the alkynyl groups have one or two (most preferably one) triple bond(s).

In addition, the expressions alkyl, alkenyl and alkynyl refer to groups, in which e.g. one or more hydrogen atoms are replaced by a halogen atom (preferably F or Cl), —COOH, —OH, —SH, —SO$_{(0-2)}$R$^4$, —NH$_2$, —NO$_2$, =O, =S, =NH, such as the 2,2,2-trichloroethyl or the trifluoromethyl group.

The expression heteroalkyl refers to an alkyl, alkenyl or alkynyl group, in which one or more (preferably 1, 2 or 3) carbon atoms are replaced by an oxygen, nitrogen, phosphorus, boron, selenium, silicon or sulfur atom (preferably oxygen, sulfur or nitrogen). The expression heteroalkyl refers furthermore to a carboxy (e.g., —C(O)—) or carboxylic acid or a group derived from a carboxylic acid, such as —C(O)—O—C(CH$_3$)$_3$, acyl, acylalkyl, alkoxycarbonyl, acyloxy, acyloxyalkyl, carboxyalkylamide or alkoxycarbonyloxy. A heteroalkyl refers additionally to in-chain or side-chain sulfoxy groups including especially —SO$_{(0-2)}$R$^4$.

Examples of heteroalkyl groups are groups of formulae R$^a$—O—Y$^a$—, R$^a$—S—Y$^a$—, R$^a$—N(R$^b$)—Y$^a$—, R$^a$—CO—Y$^a$—, R$^a$—O—CO—Y$^a$—, R$^a$—CO—O—Y$^a$—, R$^a$—CO—N(R$^b$)—Y$^a$—, R$^a$—N(R$^b$)—CO—Y$^a$—, R$^a$—O—CO—N(R$^b$)—Y$^a$—, R$^a$—N(R$^b$)—CO—Y$^a$—, R$^a$—N(R$^b$)—CO—N(R$^b$)—Y$^a$—, R$^a$—O—CO—O—Y$^a$—, R$^a$—N(R$^b$)—C(=NR$^d$)—N(R$^c$)—Y$^a$—, R$^a$—CS—Y$^a$—, R$^a$—O—CS—Y$^a$—, R$^a$—CS—O—Y$^a$—, R$^a$—CS—N(R$^b$)—Y$^a$—, R$^a$—N(R$^b$)—CS—Y$^a$—, R$^a$—O—CS—N(R$^b$)—Y$^a$—R$^a$—N(R$^b$)—CS—O—Y$^a$—, R$^a$—N(R$^b$)—CS—N(R$^c$)—Y$^a$—, R$^a$—O—CS—O—Y$^a$—, R$^a$—S—CO—Y$^a$—, R$^a$—CO—S—Y$^a$—, R$^a$—S—CO—N(R$^a$—Y$^a$—, R$^a$—N(R$^b$)—CO—S—Y$^a$—, R$^a$—S—CO—O—Y$^a$—, R$^a$—O—CO—S—Y—, R$^a$—S—CS—Y$^a$—, R$^a$—CS—S—Y$^a$—, R$^a$—S—CS—N(R$^b$)—Y$^a$—, R$^a$—N(R$^b$)—CS—S—Y$^a$—, R$^a$—S—CS—O—Y$^a$—, R$^a$—O—CS—S—Y$^a$—, whereby R$^a$ is a hydrogen atom, a C$_1$-C$_6$-alkyl-, a C$_2$-C$_6$-alkenyl- or a C$_2$-C$_6$-alkynyl group; R$^b$ is a hydrogen atom, a C$_1$-C$_6$-alkyl-, a C$_2$-C$_6$-alkenyl- or a C$_2$-C$_6$-alkynyl group; R$^c$ is a hydrogen atom, a C$_1$-C$_6$-alkyl-, a C$_2$-C$_6$-alkenyl- or a C$_2$-C$_6$-alkynyl group; R$^d$ is a hydrogen atom, a C$_1$-C$_6$-alkyl-, a C$_2$-C$_6$-alkenyl- or a C$_2$-C$_6$-alkynyl group and Y$^a$ is a direct bond, a C$_1$-C$_6$-alkylene, a C$_2$-C$_6$-alkenylene or a C$_2$-C$_6$-alkynylene group, whereby each heteroalkyl group contains at least one carbon atom and one or more hydrogen atoms can be replaced by fluorine or chlorine atoms. Specific examples of heteroalkyl groups are methoxy, trifluoromethoxy, ethoxy, n-propyloxy, isopropyloxy, tert-butyloxy, methoxymethyl, ethoxymethyl, methoxyethyl, methylamino, ethylamino, dimethylamino, diethylamino, iso-propylethylamino, methyl-aminomethyl, ethylaminomethyl, di-iso-propylaminoethyl, enolether, dimethylaminomethyl, dimethylaminoethyl, acetyl, propionyl, butyryloxy, acetyloxy, methoxycarbonyl, ethoxy-carbonyl, N-ethyl-N-methylcarbamoyl or N-methylcarbamoyl. Further examples of heteroalkyl groups are nitrile, isonitrile, cyanate, thiocyanate, isocyanate, isothiocyanate and alkylnitrile groups.

The expression cycloalkyl refers to a saturated or partially unsaturated (e.g. cycloalkenyl) cyclic group, which has one or more rings (preferably 1 or 2 or 3) that form a frame, which contains in particular 3 to 14 carbon atoms, preferably 3 to 10 (especially 3, 4, 5, 6 or 7) carbon atoms. The expression cycloalkyl further refers to groups in which one or more hydrogen atoms are replaced by fluorine, chlorine, bromine or iodine atoms or —COOH, —OH, =O, —SH, =S, —NH$_2$, =NH, —NO$_2$, alkyl or heteroalkyl groups, that is, for example, cyclic ketones such as cyclohexanone, 2-cyclohexenone or cyclopentanone. Further specific examples of cycloalkyl groups are the cyclopropyl, cyclobutyl, cyclopentyl, spiro[4,5]decanyl, norbornyl, cyclohexyl, cyclopentenyl, cyclohexadienyl, decalinyl, cubanyl, bicyclo[4.3.0]nonyl, tetraline, cyclopentylcyclohexyl, fluorocyclohexyl or the cyclohex-2-enyl group.

The expression heterocycloalkyl refers to a cycloalkyl group as defined above, in which one or more (preferably 1, 2 or 3) ring carbon atoms are replaced by an oxygen, nitrogen, silicon, selenium, phosphorus or sulfur atom (preferably oxygen, sulfur or nitrogen). A heterocycloalkyl group preferably possesses 1 or 2 rings with 3 to 10 (especially 3, 4, 5, 6 or 7) ring atoms. The expression heterocycloalkyl further refers to groups in which one or more hydrogen atoms are replaced by fluorine, chlorine, bromine or iodine atoms or —COOH, —OH, =O, —SH, =S, —NH$_2$, =NH, —NO$_2$, alkyl or heteroalkyl groups. Examples are the piperidyl, morpholinyl, urotropinyl, pyrrolidinyl, tetrahydrothiophenyl, tetrahydropyranyl, tetrahydro-furyl, oxacyclopropyl, azacyclopropyl or 2-pyrazolinyl group, as well as lactams, lactones, cyclic imides and cyclic anhydrides.

The expression alkylcycloalkyl refers to group which, in accordance with the above definitions, contain both cycloalkyl and alkyl, alkenyl or alkynyl groups, e.g. alkylcycloalkyl, alkylcycloalkenyl, alkenylcycloalkyl and alkynylcycloalkyl groups. An alkylcycloalkyl group preferably contains a cycloalkyl group which has one or two rings with 3 to 10 (especially 3, 4, 5, 6 or 7) ring carbon atoms, and one or two alkyl, alkenyl or alkynyl groups with 1 or 2 to 6 carbon atoms.

The expression heteroalkylcycloalkyl refers to alkylcycloalkyl groups as defined above, in which one or more (preferably 1, 2 or 3) ring carbon atoms and/or carbon atoms are replaced by an oxygen, nitrogen, silicon, selenium, phosphorus or sulfur atom (preferably oxygen, sulfur or nitrogen). A heteroalkylcycloalkyl group preferably possesses 1 or 2 rings with 3 to 10 (especially 3, 4, 5, 6 or 7) ring atoms and one or two alkyl, alkenyl, alkynyl or heteroalkyl groups with 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and heteroalkyl-heterocylcloalkenyl, whereby the cyclic groups are saturated or are mono-, di- or tri-unsaturated.

The expression halo or halogen is preferably fluoro, chloro, bromo or iodo, most preferably fluoro, chloro or bromo.

The expression aryl or Ar refers to an aromatic group, which has one or more rings with, in particular, 6 to 14 ring carbon atoms, preferably 6 to 10 (especially 6) ring carbon atoms. The expression aryl (or Ar) further refers to groups in which one or more hydrogen atoms are replaced by fluorine, chlorine, bromine or iodine atoms or —COOH, —OH, —SH, =NH, —NO$_2$, alkyl or heteroalkyl groups. Examples are the phenyl, naphthyl, biphenyl, anilinyl, 2-fluorophenyl, 3-nitrophenyl or 4-hydroxyphenyl group.

The expression heteroaryl refers to an aromatic group which contains one or more rings with in particular 3 to 14 ring atoms, preferably 5 to 10 (especially 5 or 6) ring atoms, and one or more (preferably 1, 2, 3 or 4) oxygen, nitrogen, phosphorus or sulfur ring atoms (preferably O, S or N). The expression heteroaryl further refers to groups in which one or more hydrogen atoms are replaced by fluorine, chlorine, bromine or iodine atoms or —COOH, —OH, —SH, =NH, —NO$_2$, alkyl or heteroalkyl groups. Examples are 4-pyridyl, 2-imidazolyl, 3-phenylpyrrolyl, thiazolyl-oxazolyl, triazolyl, tetrazolyl, isoxazolyl, indazolyl, indolyl, benzimidazolyl, pyridazinyl, quinolinyl, purinyl, carbazolyl, acridinyl, pyrimidyl, 2,3'-bifuryl, 3-pyrazolyl and isoquinolinyl groups.

The expression aralkyl refers to groups which, in accordance with the above definitions, contain both aryl and alkyl, alkenyl, alkynyl and/or cycloalkyl groups, such as arylalkyl, alkylaryl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetraline, dihydronaphthalene, indanone, phenylcyclopentyl, cumene, cyclohexylphenyl, fluorene and indane. An aralkyl group preferably contains one or two aromatic rings with 6 to 10 ring carbon atoms and one or two alkyl, alkenyl and/or alkynyl groups with 1 or 2 to 6 carbon atoms and/or a cycloalkyl group with 5 or 6 ring carbon atoms.

The expression heteroaralkyl refers to an aralkyl group as defined above, in which one or more (preferably 1, 2, 3 or 4) ring carbon atoms and/or carbon atoms are replaced by an oxygen, nitrogen, silicon, selenium, phosphorus, boron or sulfur atom (preferably oxygen, sulfur or nitrogen), i.e. it refers to groups which, in accordance with the above definitions, contain both aryl or heteroaryl, and alkyl, alkenyl, alkynyl and/or heteroalkyl and/or cycloalkyl and/or heterocycloalkyl groups. A heteroaralkyl group preferably contains one or two aromatic rings with 5 or 6 to 10 ring carbon atoms and one or two alkyl, alkenyl and/or alkynyl groups with 1 or 2 to 6 carbon atoms and/or a cycloalkyl group with 5 or 6 ring carbon atoms, whereby 1, 2, 3 or 4 of these carbon atoms are replaced by oxygen, sulfur or nitrogen atoms.

Examples are arylheteroalkyl, arylheterocycloalkyl, arylheterocycloalkenyl, arylalkylheterocycloalkyl, arylalkenyl-heterocycloalkyl, arylalkynylheterocycloalkyl, arylalkyl-heterocycloalkenyl, heteroarylalkyl, heteroarylalkenyl, heteroarylalkynyl, heteroarylhetero-alkyl, heteroarylcycloalkyl, heteroarylcycloalkenyl, heteroarylheterocycloalkyl, hetero-arylheterocycloalkenyl, heteroarylalkylcycloalkyl, heteroarylalkylheterocycloalkenyl, heteroarylheteroalkylcycloalkyl, heteroarylheteroalkylcycloalkenyl and heteroarylhetero-alkylheterocycloalkyl groups, whereby the cyclic groups are saturated or are mono-di- or tri-unsaturated. Specific examples are the tetrahydroisoquinolinyl, benzoyl, 2- or 3-ethylindolyl, 4-methylpyridino, 2-, 3- or 4-methoxyphenyl, 4-ethoxyphenyl, 2-, 3- or 4-carboxyphenylalkyl group.

The expressions cycloalkyl, hereocycloalkyl, alkylcycloalkyl, heteroalkylcycloalkyl, aryl, heteroaryl, aralkyl and heteroaralkyl further refer to groups in which one or more hydrogen atoms are replaced by fluorine, chlorine, bromine or iodine atoms or OH, =O, SH, =S, NH$_2$, =NH or NO$_2$ groups.

The expression "optionally substituted" refers to groups in which one or more hydrogen atoms are replaced e.g. by fluorine, chlorine, bromine or iodine atoms or —COOH, —OH, =O, —SH, =S, —NH$_2$, =NH, —NO$_2$, alkyl or heteroalkyl groups. This expression further refers to groups that are substituted by unsubstituted $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_8$ heterocycloalkyl, $C_6$-$C_{10}$ aryl, $C_1$-$C_8$ heteroaryl, $C_7$-$C_{12}$ aralkyl or $C_2$-$C_{11}$ heteroaralkyl groups.

Compounds of formula (I) may contain one or more centres of chirality depending on their substitution. The present invention therefore includes both all pure enantiomers and all pure diastereoisomers, and their mixtures in any ratio. In addition, the present invention also includes all cis/trans isomers of the compounds of the general formula (I) as well as mixtures thereof. In addition, the present invention includes all tautomeric forms of the compounds of formula (I).

In one embodiment, $R^1$ is a lipophilic (hydrophobic) group. In another embodiment, $R^1$ is preferably a lipophobic (hydrophilic) group.

In certain embodiments, $R^1$ is a $C_{1-10}$ alkyl group, a —$(CO)_{0-1}$—$(CH_2)_{0-6}$—$C_{3-7}$-cycloalkyl group, a —$(CO)_{0-1}$—$(CH_2)_{0-6}$-phenyl group, a —$(CO)_{0-1}$—$(CH_2)_{0-6}$-naphthyl group, a —$(CO)_{0-1}$—$(CH_2)_{0-6}$-heteroaryl group or a —$(CO)_{0-1}$—$(CH_2)_{0-6}$-heterocycloalkyl group, whereby the cycloalkyl, phenyl, naphthyl, heteroaryl or heterocycloalkyl groups may optionally be substituted. In other embodiments, $R^1$ is, e.g., $SO_{(0-2)}R^4$; $COR^4$; $CONR^4$ or is $CONR^4R^5$.

$R^2$ is preferably $C_{1-10}$-alkyl, —$(CH_2)_{0-6}$—$C_{3-7}$-cycloalkyl, $C_{1-10}$-alkyl-phenyl, $C_{1-10}$-alkyl-naphthyl, —$(CH_2)_{0-6}$—$C_{3-7}$-cycloalkyl-$(CH_2)_{0-6}$-phenyl (whereby this group also includes condensed cycloalkyl-phenyl ring systems, e.g. indane or tetrahydronaphthalene), —$(CH_2)_{0-4}$—CH$((CH_2)_{0-4}$-phenyl$)_2$, —$(CH_2)_{0-6}$-heterocycloalkyl or —$(CH_2)_{0-6}$-heteroaryl, whereby the cycloalkyl, phenyl, naphthyl, heteroaryl or heterocycloalkyl groups may optionally be substituted.

More preferably, $R^2$ is an amino acid residue, as defined in WO2004/005248, which is incorporated herein by reference in its entirety.

Most preferably, $R^2$ is an optionally substituted benzyl, phenethyl or tetrahydronaphthyl group.

$R^3$ is preferably a group of formula $CH_3$—NH—$CHR^6$—CO—NH—$CHR^7$—CO—, whereby the radicals $R^3$ and $R^7$ are defined as above, and are preferably, independently of one another, $C_{1-10}$-alkyl-, $C_{3-7}$-cycloalkyl- or $C_{1-10}$-heteroalkyl groups; in this instance, $R^6$ is most preferably a methyl group and $R^7$ a group of formula —$CH(CH_3)_2$ or —$C(CH_3)_3$.

m is preferably an integer 1.

More preferably, A-B together are a group of formula $CH_2$—CH, CH=C or CO—CH.

Specific examples of preferred compounds of the invention are provided in Tables 1-3.

It will be apparent to one of skill in the art when a compound of the invention can exist as a salt form, especially as an acid addition salt or a base addition salt. When a compound can exist in a salt form, such salt forms are included within the scope of the invention. Although any salt form may be useful in chemical manipulations, such as purification procedures, only pharmaceutically acceptable salts are useful for pharmaceutical products.

When a basic group and an acid group are present in the same molecule, a compound of formula (I) may also form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the compounds in free form and those in the form of their salts, including those salts that can be used as intermediates, for example in the purification or identification of the compounds, tautomers or tautomeric mixtures and their salts, any reference to the compounds hereinbefore and hereinafter especially the compounds of the formula I, is to be understood as referring also to the corresponding tautomers of these compounds, especially of compounds of the formula I, tautomeric mixtures of these compounds, especially of compounds of the formula I, or salts of any of these, as appropriate and expedient and if not mentioned otherwise.

Where "a compound . . . , a tautomer thereof; or a salt thereof" or the like is mentioned, this means "a compound . . . , a tautomer thereof, or a salt of the compound or the tautomer".

Any asymmetric carbon atom may be present in the (R)-, (S)- or (R,S)-configuration, preferably in the (R)- or (S)-configuration. Substituents at a ring at atoms with saturated bonds may, if possible, be present in cis- (=Z-) or trans (=E-) form. The compounds may thus be present as mixtures of isomers or preferably as pure isomers, preferably as enantiomer-pure diastereomers or pure enantiomers.

The present invention also relates to pro-drugs of a compound of formula (I) that convert in vivo to the compound of formula (I) as such. Any reference to a compound of formula (I) is therefore to be understood as referring also to the corresponding pro-drugs of the compound of formula (I), as appropriate and expedient.

The compounds of formula (I) have valuable pharmacological properties and are useful in the treatment of kinase dependent diseases, e.g., as drugs to treat proliferative diseases.

Pharmaceutically acceptable salts include, when appropriate, pharmaceutically acceptable base addition salts and acid addition salts, for example, metal salts, such as alkali and alkaline earth metal salts, ammonium salts, organic amine addition salts, and amino acid addition salts, and sulfonate salts. Acid addition salts include inorganic acid addition salts such as hydrochloride, sulfate and phosphate, and organic acid addition salts such as alkyl sulfonate, arylsulfonate, acetate, maleate, fumarate, tartrate, citrate and lactate. Examples of metal salts are alkali metal salts, such as lithium salt, sodium salt and potassium salt, alkaline earth metal salts such as magnesium salt and calcium salt, aluminum salt, and zinc salt. Examples of ammonium salts are ammonium salt and tetramethylammonium salt. Examples of organic amine addition salts are salts with morpholine and piperidine. Examples of amino acid addition salts are salts with glycine, phenylalanine, glutamic acid and lysine. Sulfonate salts include mesylate, tosylate and benzene sulfonic acid salts.

Examples of pharmacologically acceptable salts of compounds of formula (I) are salts of physiologically acceptable mineral acids, such as hydrochloric acid, sulfuric acid and phosphoric acid; or salts of organic acids, such as methanesulfonic acid, p-toluenesulfonic acid, lactic acid, formic acid, acetic acid, trifluoroacetic acid, citric acid, succinic acid, fumaric acid, maleic acid and salicylic acid. Compounds of formula (I) may be solvated, in particular hydrated. Hydration may arise e.g. during the preparation process or as a consequence of the hygroscopic nature of the initially water-free compounds of formula (I).

The pharmaceutical compositions according to the present invention contain at least one compound of formula (I) as active ingredient and optionally carriers and/or adjuvants.

The prodrugs (e.g. R. B. Silverman, Medizinische Chemie, V C H Weinheim, 1995, chapter 8, pp 361ff), which are likewise an object of the present invention, consist of a compound of formula (I( ) and at least one pharmacologically acceptable protecting group, which is cleaved under physiological conditions, e.g. a hydroxy, alkoxy, aralkyloxy, acyl or acyloxy group, such as a methoxy, ethoxy, benzyloxy, acetyl or acetyloxy group.

The usage of these active ingredients in producing medicaments is also an object of the present invention. In general, compounds of formula (I) are administered using known, acceptable methods, either singly or in combination with any other therapeutic agent. Administration may be effected e.g. in one of the following ways: orally, e.g. as dragées, coated tablets, pills, semi-solids, soft or hard capsules, solutions, emulsions or suspensions; parenterally, e.g. as an injectable solution; rectally as suppositories; by inhalation, e.g. as a powder formulation or spray, transdermally or intra-nasally. To produce such tablets, pills, semi-solids, coated tablets, dragées and hard gelatin capsules, the therapeutically employable product may be mixed with pharmacologically inert, inorganic or organic carriers for medicaments, e.g. with lactose, sucrose, glucose, gelatin, malt, silica gel, starch or derivatives thereof, talc, stearic acid or salts thereof, dry skimmed milk and the like. To produce soft capsules, carriers for medicaments, such as vegetable oils, petroleum, animal or synthetic oils, wax, fat, polyols, may be used. To produce liquid solutions and syrups, carriers for medicaments, such as water, alcohols, aqueous salt solution, aqueous dextrose, polyols, glycerol, vegetable oils, petroleum, animal or synthetic oils, may be used. For suppositories, carriers for medicaments, such as vegetable oils, petroleum, animal or synthetic oils, wax, fat and polyols, may be used. For aerosol formulations, compressed gases that are appropriate for this purpose may be used, such as oxygen, nitrogen and carbon dioxide. The pharmaceutically acceptable agents may also contain preserving and stabilizing additives, emulsifiers, sweeteners, aromatics, salts to modify the osmotic pressure, buffers, coating additives and antioxidants.

Combinations with other therapeutic agents may contain other active ingredients, e.g. taxanes, which are customarily used to prevent and/or treat tumour diseases. Taxanes include compounds such as paclitaxel and docetaxel. Paclitaxel is marketed as TAXOL; and docetaxel is marketed as TAXOTERE. Other taxanes include vinorelbine and the epothilones, such as epothilone B and patupilone.

In other embodiments, the invention provides a kit including any of the compounds of the present invention. In a related embodiment, the kit further includes a pharmaceutically acceptable carrier or excipient of any of these compounds. In another related embodiment, the compounds of the invention, present in the kit, are in a unit dose. In still another related embodiment, the kit further includes instructions for use in administering to a subject.

Compounds of formula (I) may be produced by the processes described in K. Rossen, J. Sager, L. M. DiMichele; Tetrahedron Letters, Vol. 38, No. 18, pp 3183-3186, 1997 and in A. v. Zychlinski and 1. Ugi, HETEROCYCLES, Vol. 49, pp 29-32, 1998, by reacting the corresponding BOC-protecting dipeptides with the corresponding other starting materials. The BOC-protecting groups can then be removed under standard conditions with trifluoroacetic acid. Purification may take place by HPLC. An exemplary synthesis method is provides as follows.

General Synthesis of Series A

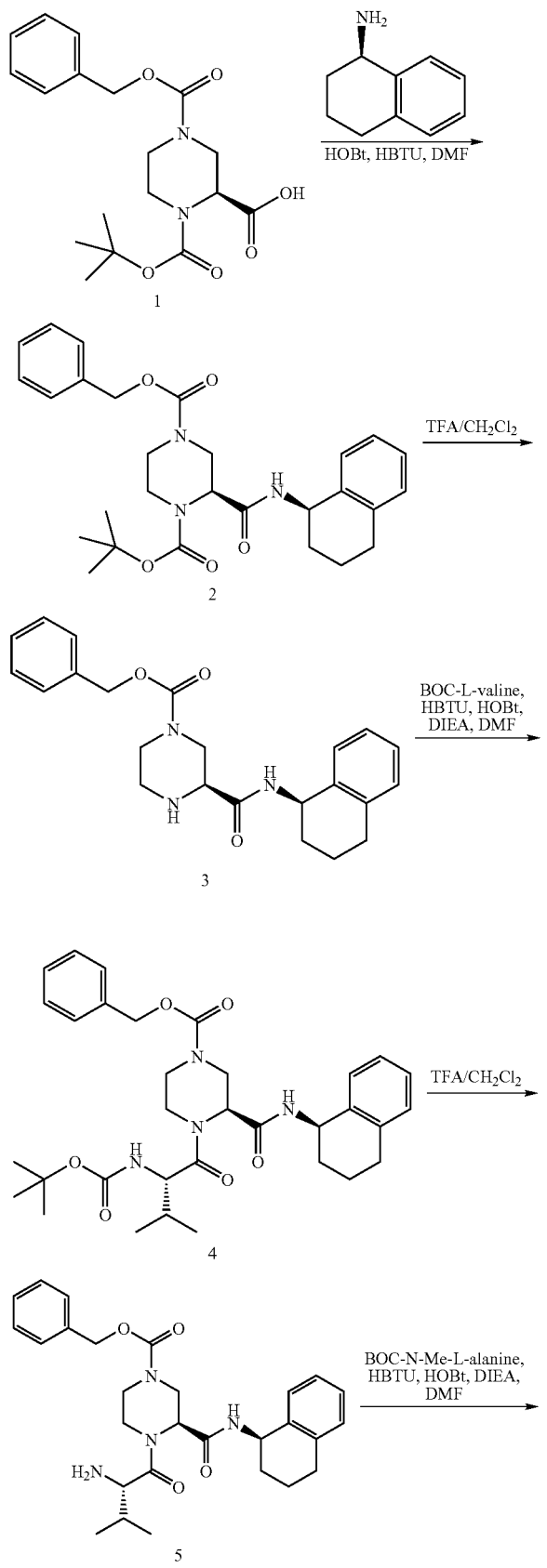

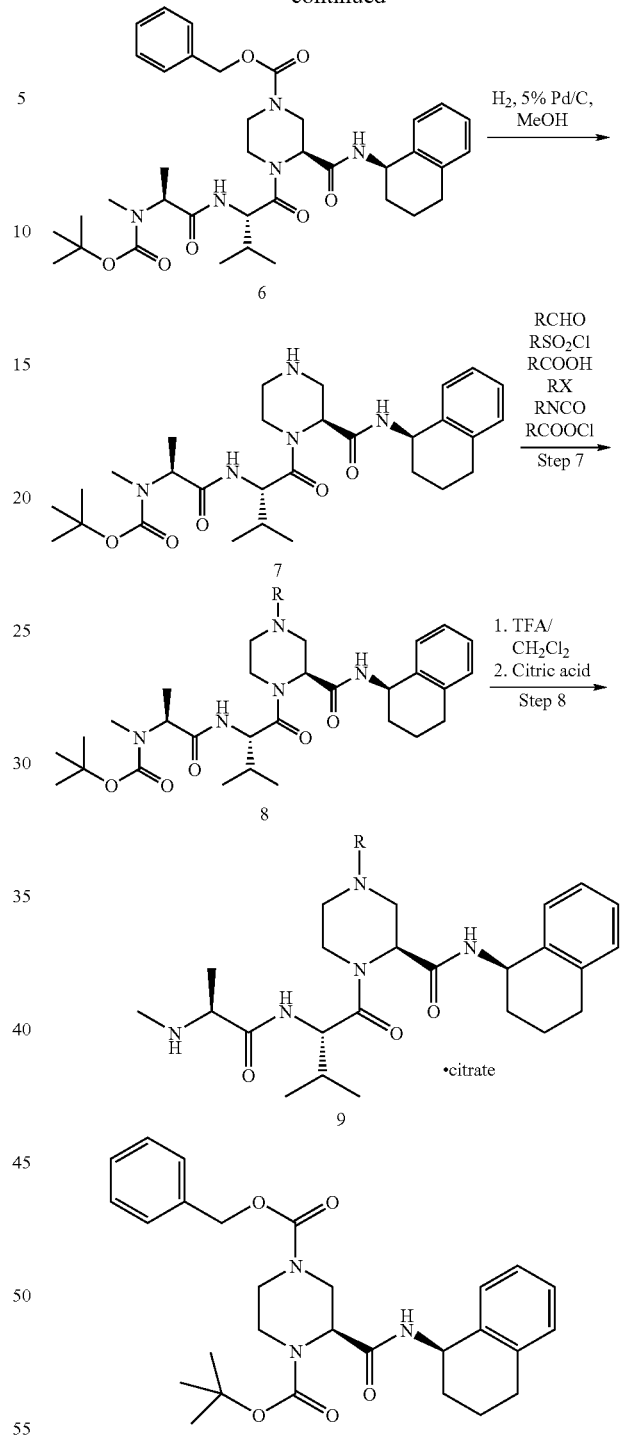

4-Benzyl 1-tert-butyl (2S)-2-{[(1R)-1,2,3,4-tetrahydro-1-naphthalenyl-amino]carbonyl}-1,4-piperazinedicarboxylate (2)

(2S)-4-[(benzyloxy)carbonyl]-1-(tert-butoxycarbonyl)-2-piperazinecarboxylic acid (1, 17.33 g, 47.5 mmol) is dissolved in DMF (800 mL), to which is added diisopropylethylamine (DIEA, 41.5 mL, 0.24 mol). This mixture is stirred at RT for 1.5 h. R-(−)-1,2,3,4-tetrahydro-1-naphthylamine (7.00 g, 47.5 mmol) is added, and stirring continued for a further hour. O-(Benzotriazol-1-yl)-N,N,N',N'-tetramethyluronium hexafluorophosphate (HBTU, 19.84 g, 52.3 mmol)

and 1-hydroxybenzotriazole hydrate (HOBt, 7.07 g, 52.3 mmol) are also added and the entire mixture stirred overnight at RT. The reaction mixture is then diluted with EtOAc (1.2 L) and washed sequentially with 1 M citric acid, brine, sat. NaHCO$_3$, brine, water and brine (1 L of each solution). The EtOAc layer is then dried with Na$_2$SO$_4$, filtered, and the solvent removed under reduced pressure to afford a crude off-white solid (23.34 g). This material is purified by flash chromatography on silica gel (CH$_2$Cl$_2$ as eluent initially, followed by 5% Et$_2$O/CH$_2$Cl$_2$ to elute the desired product). The desired coupled product 6 is isolated as a white foam (20.37 g, 87% yield): $^1$H NMR δ (CDCl$_3$) 7.27-7.42 (m, 5H), 7.06-7.19 (m, 4H), 6.10 (brs, 1H), 5.11-5.25 (br m, 3H), 4.46-4.75 (br m, 2H), 3.77-4.02 (br m, 2H), 3.00-3.31 (br m, 3H), 2.68-2.84 (m, 2H), 1.97-2.07 (br m, 1H), 1.69-1.84 (br m, 3H), 1.43 (s, 9H). LCMS (APCl$^+$) 494.8 (MH$^+$), 438.5 (MH$^+$-tBu), 394.4 (MH$^+$-BOC).

(36.0 mL, 0.21 mol), HBTU (17.19 g, 45.3 mmol) and HOBt (6.12 g, 45.3 mmol) in DMF (700 mL) under the same conditions as in step 1 above. Purification is carried out by flash chromatography on silica gel (CH$_2$Cl$_2$ as eluent initially, followed by 10% Et$_2$O/CH$_2$Cl$_2$ to elute the desired product). The desired coupled product 4 is isolated as a white foam (15.51 g, 64% yield): $^1$H NMR δ (CDCl$_3$) 6.99-7.64 (m, 9H), 5.99-6.34 (br m, 1H), 2.68-5.26 (br m, 11H), 1.51-2.15 (br m, 6H), 1.42 (s, 9H), 1.15 (s, 3H), 0.64-1.02 (br m, 5H); LCMS (APCl$^+$) 594.2 (MH$^+$), 537.9 (MH$^+$-tBu), 493.7 (MH$^+$-BOC, 100%).

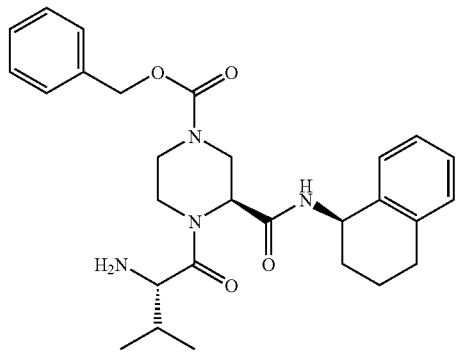

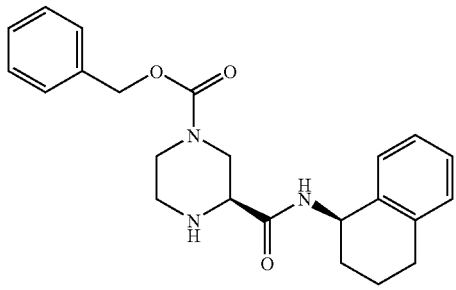

Benzyl(3S)-3-{[(1R)-1,2,3,4-tetrahydro-1-naphthalenylamino]carbonyl}-1-piperazinecarboxylate (3)

The amide 2 (20.35 g, 41.2 mmol) is dissolved in a mixture of CH$_2$Cl$_2$ (600 mL) and TFA (153 ml, 2.06 mol). The flask is sealed under N$_2$ and the mixture stirred overnight at RT. All solvents are removed under reduced pressure to afford an oil which is dissolved in CH$_2$Cl$_2$ (500 mL), then washed with sat. NaHCO$_3$ (2×500 mL) and brine (500 mL). The CH$_2$Cl$_2$ solution is dried (Na$_2$SO$_4$), filtered, and the solvent removed under reduced pressure to give the desired product 7 as an off-white foam (16.21 g, 100% yield): $^1$H NMR δ (CDCl$_3$) 7.07-7.39 (m, 10H), 5.10-5.21 (m, 3H), 4.18-4.26 (m, 1H), 3.78-3.88 (m, 1H), 3.39 (dd, J=9.2, 3.6 Hz, 1H), 2.70-3.19 (m, 6H), 1.97-2.07 (m, 1H), 1.73-1.86 (m, 3H); LCMS (APCl$^+$) 394.4 (MH$^+$, 100%).

Benzyl (3S)-4-[(2S)-2-amino-3-methylbutanoyl]-3-{[(1R)-1,2,3,4-tetrahydro-1-naphthalenylamino]carbonyl}-1-piperazinecarboxylate (5)

Compound 4 (15.50 g, 26.2 mmol) is BOC-deprotected using TFA (97 mL, 1.31 mol) in CH$_2$Cl$_2$ (500 mL) under the same conditions as for step 2. After workup, the desired free amine 5 is obtained as an off-white foam (12.57 g, 97% yield): $^1$H NMR δ (CDCl$_3$) 7.28-7.42 (m, 5H), 7.03-7.19 (m, 4H), 6.07-6.35 (br m, 1H), 5.09-5.27 (br m, 3H), 3.68-4.81 (br m, 3H), 2.66-3.53 (br m, 6H), 1.45-2.04 (br m, 8H), 0.74-1.00 (br m, 1H); LCMS (APCl$^+$) 493.7 (MH$^+$, 100%).

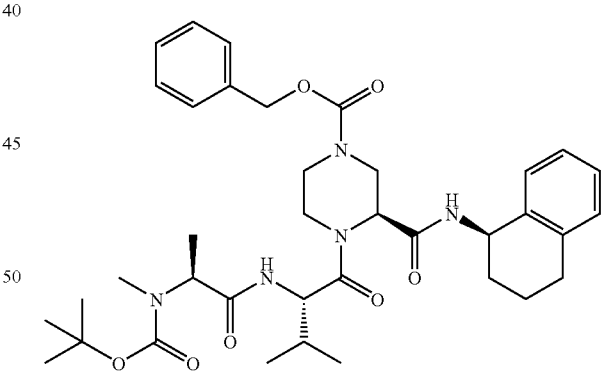

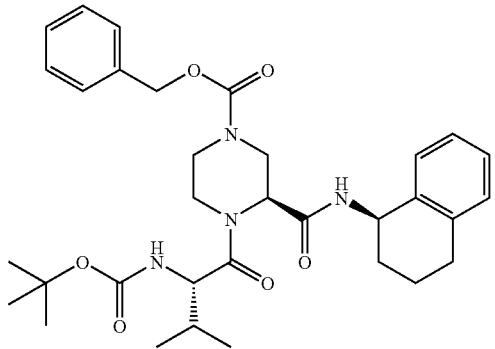

Benzyl (3S)-4-{(2S)-2-[(tert-butoxycarbonyl)amino]-3-methylbutanoyl}-3-{[(1R)-1,2,3,4-tetrahydro-1-naphthalenylamino]carbonyl}-1-piperazinecarboxylate (4)

The deprotected piperazine 3 (16.20 g, 41.2 mmol) is coupled with BOC-L-valine (8.95 g, 41.2 mmol) using DIEA Benzyl (3S)-4-[(2S)-2-({(2S)-2-[(tert-butoxycarbonyl)(methyl)amino]propanoyl}amino)-3-methylbutanoyl]-3-{[(1R)-1,2,3,4-tetrahydro-1-naphthalenylamino]carbonyl}-1-piperazinecarboxylate (6)

Amine 5 (12.57 g, 25.5 mmol) is then coupled with BOC-N-methyl-L-alanine (5.18 g, 25.5 mmol) using DIEA (22.3 mL, 0.13 mol), HBTU (10.64 g, 28.1 mmol) and HOBt (3.79 g, 28.1 mmol) in DMF (550 mL) under the same conditions as in step 1 above. Purification is carried out by flash chromatography on silica gel (CH$_2$Cl$_2$ as eluent initially, followed by 50% Et$_2$O/CH$_2$Cl$_2$ to elute the desired product). The desired coupled product 6 is isolated as a white foam (15.30 g, 89% yield): $^1$H NMR δ (CDCl$_3$) 7.28-7.38 (br m, 5H), 7.03-7.19

(br m, 4H), 6.73 (br s, 1H), 6.02-6.35 (br m, 1H), 5.05-5.26 (br m, 4H), 3.84-4.82 (br m, 5H), 2.68-3.56 (br m, 9H), 1.70-2.07 (br m, 5H), 1.47 (s, 9H), 0.60-1.33 (br m, 8H); LCMS (APCl⁺) 679.0 (MH⁺), 579.0 (MH⁺-BOC, 100%); HPLC (C18 column) 99.4%.

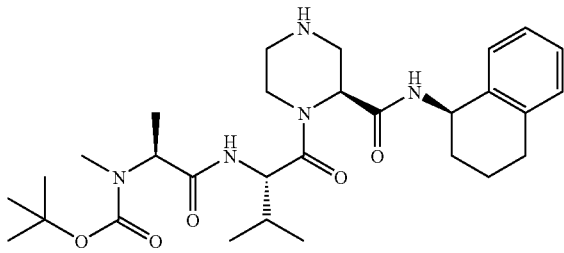

tert-Butyl methyl[(1S)-1-methyl-2-({(1S)-2-methyl-1-[((2S)-2-{[(1R)-1,2,3,4-tetrahydro-1-naphthalenylamino]carbonyl}piperazinyl)carbonyl]propyl}amino)-2-oxoethyl]carbamate (7)

Compound 6 (13.02 g, 19.2 mmol) is dissolved in MeOH (600 mL), to which is added 5% Pd/C (1.80 g). This mixture is stirred in a pressure vessel under an atmosphere of hydrogen (40 psi) for 2 h. The catalyst is then removed by filtration over celite and the solvent removed from the resulting filtrate to afford a crude oil which is purified by flash chromatography on silica gel (5% MeOH/CH₂Cl₂). The desired product 7 is obtained as a white foam (9.71 g, 93% yield): ¹H NMR δ (CDCl₃) 7.02-7.20 (m, 4H), 6.71 (br s, 1H), 6.37 (br d, J=8.8 Hz, 1H), 4.16-5.13 (br m, 4H), 3.10-3.71 (br m, 3H), 2.64-2.84 (br m, 7H), 1.58-2.11 (br m, 7H), 1.46 (s, 9H), 1.30 (d, J=7.1 Hz, 2H), 0.86-1.02 (br m, 3H), 0.75 (d, J=6.7 Hz, 2H), 0.53 (br d, J=6.7 Hz, 2H); LCMS (APCl⁺) 544.9 (MH⁺), 444.6 (MH⁺-BOC), 260.2 (MH⁺-dipeptide, 100%); HPLC (C8 column) 95.2%.

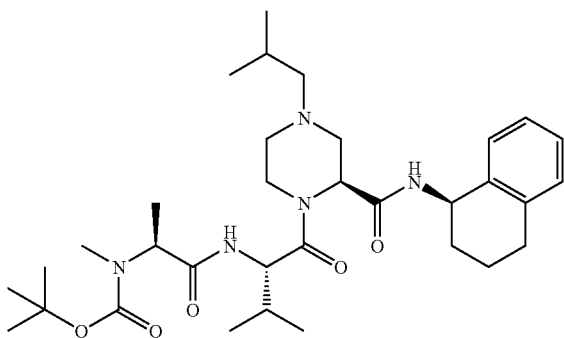

Example of a procedure for the reductive amination of 7 with aldehydes.

tert-Butyl(1S)-2-({(1S)-1-[((2S)-4-isobutyl-2-{[(1R)-1,2,3,4-tetrahydro-1-naphthalenylamino]carbonyl}piperazinyl)carbonyl]-2-methylpropyl}amino)-1-methyl-2-oxoethyl(methyl)carbamate (8, R=isobutyl)

Intermediate 7 (250 mg, 0.46 mmol) is dissolved in 1,2-dichloroethane (4 mL), to which is added iso-butyraldehyde (63 μL, 0.69 mmol) and NaBH(OAc)₃ (146 mg, 0.69 mmol). This mixture is stirred under N₂ at RT overnight. LCMS at this point shows a small amount of unreacted starting material so further quantities of iso-butyraldehyde (63 μL, 0.69 mmol) and NaBH(OAc)₃ (146 mg, 0.69 mmol) are added. After a further 4 h. of stirring at RT the reaction mixture is diluted with CH₂Cl₂ (50 mL) and then washed with water (50 mL), brine (50 mL) and dried (Na₂SO₄). After filtration, the solvent is removed under reduced pressure to afford an oil which is purified by flash chromatography on silica gel (10-50% Et₂O/CH₂Cl₂). The title compound is isolated as a white foam (255 mg, 92% yield): ¹H NMR δ (CDCl₃) 6.72-7.27 (m, 5H), 4.37-5.24 br m, 5H), 3.26-3.90 (br m, 2H), 2.67-2.96 (br m, 6H), 1.62-2.19 (m, 1H), 1.48 (s, 9H), 1.23-1.34 (m, 3H), 0.69-0.99 (m, 12H); LCMS (APCl⁺) 601.3 (MH⁺, 100%).

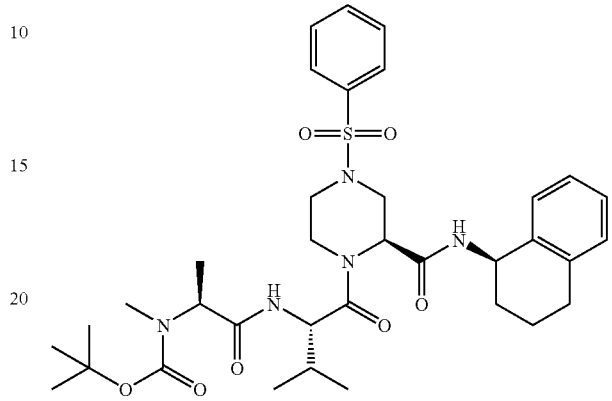

Example of a procedure for the reaction of 7 with sulfonyl chlorides tert-Butyl methyl[(1S)-1-methyl-2-({(1S)-2-methyl-1-[((2S)-4-(phenylsulfonyl)-2-{[(1R)-1,2,3,4-tetrahydro-1-naphthalenylamino]carbonyl}piperazinyl)carbonyl]propyl}amino)-2-oxoethyl]carbamate (8, R=benzenesulfonyl)

Intermediate 7 (200 mg, 0.37 mmol) is dissolved in dry CH₂Cl₂ (4 mL) and the flask sealed under N₂. DIEA (96 μL, 0.56 mmol) is added, followed by benzenesulfonyl chloride (46 μL, 0.36 mmol), then the mixture stirred at RT for 2 h. The reaction is subsequently diluted with CH₂Cl₂ (50 mL) and washed with sat. NaHCO₃ (50 mL), brine (50 mL) and dried (Na₂SO₄). After filtration, the solvent is removed under reduced pressure to afford an oil which is purified by flash chromatography on silica gel (25% Et₂O/CH₂Cl₂). The title compound is isolated as a colourless glass (216 mg, 86% yield): ¹H NMR δ (CDCl₃) 7.51-7.86 (m, 5H), 7.03-7.25 (m, 4H), 6.69 (v br s, 1H), 6.04 (br d, J=8.2 Hz, 1H), 5.16-5.25 (m, 1H), 4.29-4.75 (br m, 3H), 3.47-4.21 (br m, 3H), 2.69-2.88 (br m, 5H), 2.38-2.67 (m, 2H), 1.81-2.09 (m, 5H), 1.55 (s, 3H), 1.46 (s, 9H), 1.23-1.31 (br m, 2H), 0.84-0.92 (br m, 3H), 0.76 (d, J=6.7 Hz, 2H); LCMS (APCl⁺) 685.6 (MH⁺, 100%).

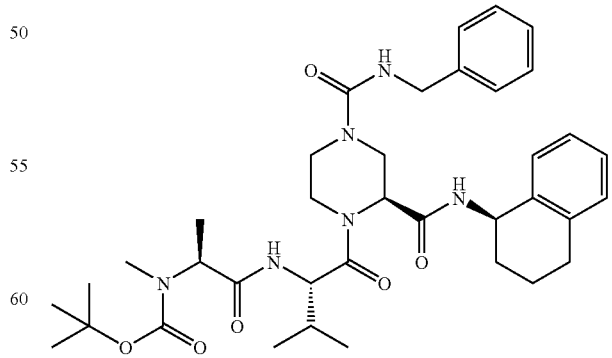

Example of a procedure for the reaction of 7 with isocyanates tert-Butyl (1S)-2-({(2S)-4-[(benzylamino)carbonyl]-2-{[(1R)-1,2,3,4-tetrahydro-1-naphthalenylamino]

carbonyl}piperazinyl)carbonyl]-2-methylpropyl}amino)-1-methyl-2-oxoethyl(methyl)carbamate (8, R=benzyl carbamoyl)

Intermediate 7 (133 mg, 0.245 mmol) is dissolved in anhydrous $CH_2Cl_2$ (5 mL), to which is added benzyl isocyanate (32 µL, 0.258 mmol). The solution is stirred at room temperature for 16 h after which time more benzyl isocyanate (10 µL, 0.08 mmol) is added and the solution is stirred for a further 5 h at room temperature. The solvent is removed under reduced pressure to afford an oil which is purified by flash chromatography on silica gel (95:5 $CH_2Cl_2$/MeOH). The title compound is isolated as a white foam (152 mg, 92% yield): $^1$H NMR δ ($CDCl_3$) 6.05-7.90 (m, 11H), 3.82-5.24 (m, 9H), 2.60-3.20 (m, 8H), 1.60-2.12 (m, 5H), 1.49 and 1.47 (s, 9H total), 1.24-1.34 (m, 3H), 1.11 (d, 1H, J=7 Hz), 1.02 (d, 2H, J=6.7 Hz), 0.75 (d, 2H, J=6.7 Hz), 0.55 (br d, 2H, J=6.1 Hz); LCMS ($APCl^+$) 678.6 ($MH^+$, 100%).

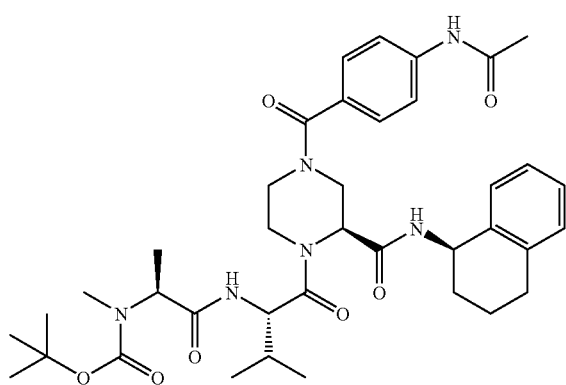

Example of a procedure for the reaction of 11 with carboxylic acids tert-Butyl (1S)-2-({(1S)-1-[((2S)-4-[4-(acetylamino)benzoyl]-2-{[(1R)-1,2,3,4-tetrahydro-1-naphthalenylamino]carbonyl}piperazinyl)carbonyl]-2-methylpropyl}amino)-1-methyl-2-oxoethyl(methyl)carbamate[8, R=4-(acetylamino)benzoyl]

Intermediate 7 (191 mg, 0.351 mmol) is dissolved in DMF (10 mL), to which is added DIEA (0.305 mL, 1.75 mmol). This mixture is stirred at room temperature for 0.5 h. 4-Acetamidobenzoic acid (66 mg, 0.368 mmol) is added, and stirring is continued for continued 1 h. HOBt (52 mg, 0.385 mmol) and HBTU (146 mg, 0.385 mmol) are then added and the entire mixture is stirred at room temperature for 2 h. The reaction mixture is diluted with EtOAc (100 mL) and washed sequentially with 1 M citric acid, brine, sat. $NaHCO_3$, brine, water and brine. The EtOAc layer is then dried with $MgSO_4$, filtered, and the solvent removed at room temperature under reduced pressure to afford a colorless gum. This material is purified by flash chromatography on silica gel (EtOAc) to give the title compound as a white foam (211 mg, 85% yield): $^1$H NMR δ ($CDCl_3$) 6.40-7.62 (m, 11H), 4.25-5.30 (m, 5H), 3.93 ("br d", 1H, $J_{obs}$=11.9 Hz), 3.47 ("br id", 1H, $J_{obs}$=11.4, 3 Hz), 2.65-3.30 (br m, 7H), 1.70-2.22 (br m, 8H), 1.48 and 1.46 (s, 9H total), 1.28-1.34 (m, 3H), 0.60-1.12 (br m, 7H); LCMS ($APCl^+$) 706.7 ($MH^+$, 100%).

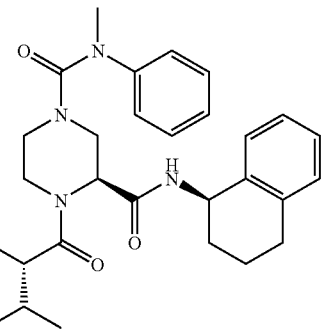

Example of a procedure for the reaction of 7 with carbamoyl chlorides tert-Butylmethyl[(1S)-1-methyl-2-({(1S)-2-methyl-1-[((2S)-4-[(methylanilino)carbonyl]-2-{[(1R)-1,2,3,4-tetrahydro-1-naphthalenylamino]carbonyl}piperazinyl)carbonyl]propyl}amino)-2-oxoethyl]carbamate (8, R=N-methyl-N-phenyl carbamoyl)

Intermediate 7 (175 mg, 0.322 mmol) is dissolved in anhydrous $CH_2Cl_2$ (15 mL), to which DIEA (70 µL, 0.40 mmol) is added. The solution is cooled to 0° C. and N-methyl-N-phenylcarbamoyl chloride (66 mg, 0.39 mmol) is added, the solution is subsequently warmed to room temperature for 4 h. N-Methyl-N-phenylcarbamoyl chloride (66 mg, 0.39 mmol) and DIEA (70 µL, 0.40 mmol) are added and the solution is stirred at room temperature for 15 h at room temperature. The solution is diluted with $CH_2Cl_2$ (50 mL) and washed with sat. $NaHCO_3$ and brine. The solution is dried ($MgSO_4$), filtered, and the solvent removed under reduced pressure to give the crude product as an oil. This material is purified by flash chromatography on silica gel (0-5% MeOH/$CH_2Cl_2$). The title compound is isolated as a white foam (168 mg, 77% yield): $^1$H NMR δ ($CDCl_3$) 6.60-7.60 (m, 10H), 4.19-5.20 (m, 5H), 3.62 ("br d", 1H, $J_{obs}$=13.2 Hz), 3.52 ("br d" 1H, $J_{obs}$=13.4 Hz), 2.56-3.28 (m, 10H), 1.72-2.10 (m, 5H), 1.47 and 1.45 (s, 9H total), 1.24-1.32 (br m, 3H), 0.88-1.12 (m, 2H), 1.09 (br d, 1H, J=6.7 Hz), 0.90 (dd, 2H, J=7.0, 2.6 Hz), 0.78 (br d, 2H, J=6.7 Hz), 0.66 (br d, 2H, 6.7 Hz; LCMS ($APCl^+$) 678.6 ($MH^+$, 100%).

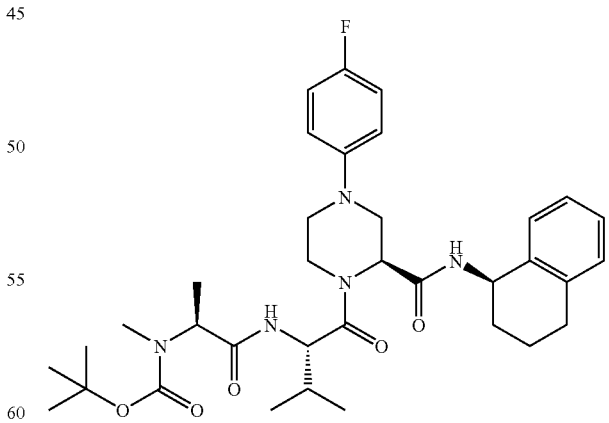

Example of a procedure for the reaction of 7 with boronic acids tert-Butyl (1S)-2-({(1S)-1-[((2S)-4-(4-fluorophenyl)-2-{[(1R)-1,2,3,4-tetrahydro-1-naphthalenylamino]carbonyl}piperazinyl)carbonyl]-2-methylpropyl}amino)-1-methyl-2-oxoethyl(methyl)carbamate (8, R=4-fluorophenyl)

Intermediate 7 (486 mg, 0.89 mmol), 4-fluorophenylboronic acid (625 mg, 4.47 mmol), Cu(OAc)$_2$ (406 mg, 2.24 mmol) and TEA (451 mg, 4.47 mmol) are all weighed into a flask, then dissolved in dry CH$_2$Cl$_2$ (20 mL). This mixture is stirred for 24 h. at room temperature, at which point some of the desired product had formed by LCMS. A further portion of boronic acid (625 mg, 4.47 mmol) is added and the mixture allowed to stir for a further 24 h, making the desired product the major peak, along with unreacted starting material. This reaction mixture is concentrated under reduced pressure, then loaded directly onto a plug of silica which is eluted with 10% Et$_2$O/CH$_2$Cl$_2$ to isolate the desired product. Unreacted starting material remains at the column baseline under these conditions. The title compound is isolated as a off-white foam (188 mg, 33% yield): $^1$H NMR δ (CDCl$_3$) 6.92-7.42 (m, 8H), 6.74 (v br s, 1H), 6.09 (br d, J=8.4 Hz, 1H), 3.97-5.27 (br m, 6H), 3.35-3.56 (br m, 2H), 2.62-3.16 (br m, 7H), 1.65-2.14 (m, 5H), 1.47 (s, 9H), 1.31 (br d, J=7.1 Hz, 2H), 1.14 (br d, J=7.1 Hz, 1H), 0.98 (brt, J=7.3 Hz, 2H), 0.79 (br d, J=6.7 Hz, 2H), 0.61 (br d, J=6.7 Hz, 2H); LCMS (APCl$^+$) 639.4 (MH$^+$, 100%).

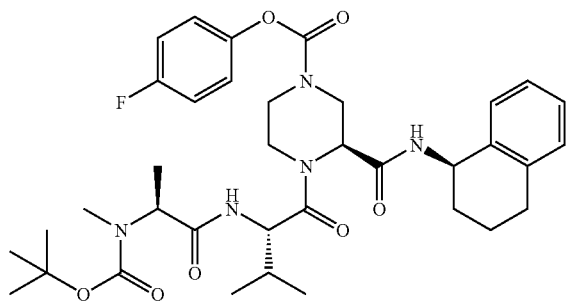

Example of a procedure for the reaction of 11 with chloroformates

4-Fluorophenyl (3S)-4-[(2S)-2-({(2S)-2-[(tert-butoxycarbonyl)(methyl)amino]-propanoyl}amino)-3-methylbutanoyl]-3-{[(1R)-1,2,3,4-tetrahydro-1-naphthalenyl-amino]carbonyl}-1-piperazinecarboxylate (8, R=4-fluorophenyloxycarbonyl)

Intermediate 7 (200 mg, 0.37 mmol) is dissolved in dry CH$_2$Cl$_2$ (4 mL) and the flask sealed under N$_2$. DIEA (96 μL, 0.56 mmol) is added, followed by benzenesulfonyl chloride (46 μL, 0.36 mmol), then the mixture stirred at RT for 2 h. The reaction is subsequently diluted with CH$_2$Cl$_2$ (50 mL) and washed with sat. NaHCO$_3$ (50 mL), brine (50 mL) and dried (Na$_2$SO$_4$). After filtration, the solvent is removed under reduced pressure to afford an oil which is purified by flash chromatography on silica gel (20% Et$_2$O/CH$_2$Cl$_2$). The title compound is isolated as a colourless glass (146 mg, 58% yield): $^1$H NMR δ (CDCl$_3$) 6.97-7.23 (m, 8H), 6.74 (v br s, 1H), 6.12-6.29 (br m, 1H), 5.08-2.25 (m, 2H), 3.90-4.86 (br m, 5H), 2.89-3.77 (br m, 4H), 2.66-2.83 (br m, 5H), 1.89-2.10 (br m, 2H), 1.68-1.88 (br m, 3H), 1.47 (s, 9H), 1.28-1.36 (br m, 2H), 0.57-1.05 (br m, 6H); LCMS (APCl$^+$) 683.7 (MH$^+$, 100%).

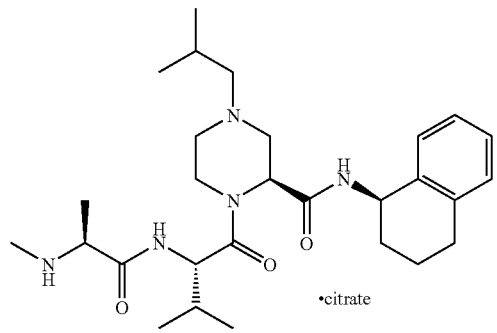

Compound A (S)-4-Isobutyl-1-[(S)-3-methyl-2-((S)-2-methylamino-propionylamino)-butyryl]-piperazine-2-carboxylic acid [(1R)1,2,3,4-tetrahydro-naphthalen-1-yl)]-amide (9, R=isobutyl, Compound A).

tert-Butyl (1S)-2-({(1S)-1-[((2S)-4-isobutyl-2-{[(1R)-1,2,3,4-tetrahydro-1-naphthalenylamino]carbonyl}piperazinyl)carbonyl]-2-methylpropyl}amino)-1-methyl-2-oxoethyl(methyl)carbamate (8, R=isobutyl) (250 mg, 0.42 mmol) is dissolved in a mixture of CH$_2$Cl$_2$ (7 mL) and TFA (1.55 ml). This mixture is stirred overnight under N$_2$ at RT. All solvent is removed under reduced pressure to afford an oil which is dissolved in CH$_2$Cl$_2$ (50 mL), then washed with sat. NaHCO$_3$ (50 mL) and brine (50 mL). The CH$_2$Cl$_2$ solution is dried (Na$_2$SO$_4$), filtered, and the solvent removed under reduced pressure to give the title compound as a white foam (157 mg, 73% yield). This foam (150 mg, 0.30 mmol) is dissolved in a mixture of EtOAc (10 mL) and MeOH (2 mL) and then anhydrous citric acid (58 mg, 0.30 mmol) added. The mixture is stirred for 1 h. at RT then the solvent removed under reduced pressure to give a white solid which is taken up in a minimal amount of water (ca 2-3 mL) and filtered. This solution is freeze-dried to afford the corresponding citrate as a fluffy white solid (193 mg): $^1$H NMR δ (d$_6$-DMSO) 10.30 (br s, 4H), 8.39-8.64 (m, 1H), 8.09-8.19 (m, 1H), 7.05-7.30 (m, 4H), 4.55-5.03 (br m, 3H), 3.00-4.20 (br m, 7H), 2.63-2.82 (br m, 3H), 2.46 (s, 3H), 1.78-2.18 (m, 7H), 1.63-1.76 (br m, 3H), 1.28-1.32 (br m, 3H), 0.79-0.96 (br m, 12H); $^{13}$C NMR δ (d$_6$-DMSO) 176.5, 171.1, 170.7, 170.3, 169.0, 168.8, 168.5, 168.0, 137.2, 137.0; 137.0, 128.6, 128.5, 128.4, 128.0, 126.6, 126.5, 125.8, 125.6, 71.2, 65.6, 56.3, 54.6, 53.5, 53.4, 52.3, 46.5, 44.0, 43.3, 31.2, 31.2, 29.7, 29.3, 28.6, 24.9, 20.5, 20.4, 20.4, 20.3, 20.0, 19.9, 19.3, 19.2, 17.5, 17.4, 16.2; LCMS (APCl$^+$) 500.9 (MH$^+$, 100%); HPLC(C18 column) 98.1%; HRMS calc. for MH$^+$ C$_{28}$H$_{46}$N$_5$O$_3$ 500.3601, found 500.3601.

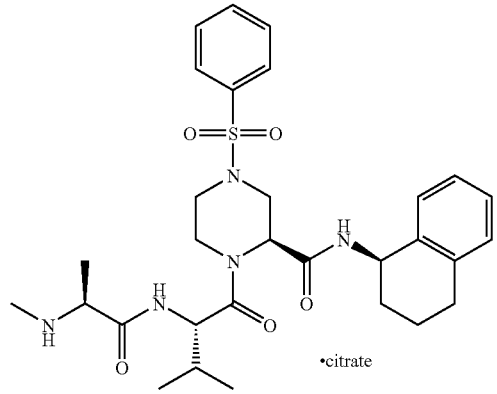

Compound B (S)-4-Benzenesulfonyl-1-[(S)-3-methyl-2-((S)-2-methylamino-propionylamino)-butyryl]-piperazine-2-carboxylic acid [(1R)-1,2,3,4-tetrahydro-naphthalen-1-yl]-amide (9, R=benzenesulfonyl, Compound B): which may be prepared following the procedure for Compound A.

Compound C

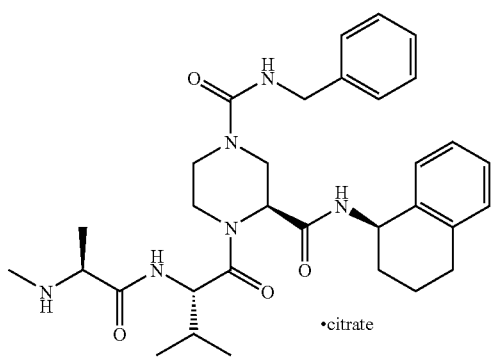

(S)-4-[(S)-3-Methyl-2-((S)-2-methylamino-propionylamino)-butyryl]-piperazine-1,3-dicarboxylic acid 1-benzylamide 3-{[(1R)-1,2,3,4-tetrahydro-naphthalen-1-yl]}-amide] (9, R=benzyl carbamoyl, Compound C): which may be prepared following the procedure for Compound A.

Compound D

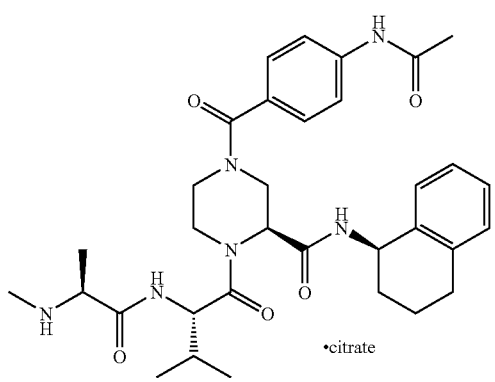

(S)-4-(4-Acetylamino-benzoyl)-1-[(S)-3-methyl-2-((S)-2-methylamino-propionylamino)-butyryl]-piperazine-2-carboxylic acid (1,2,3,4-tetrahydro-naphthalen-1-yl)-amide (9, R=4-(acetylamino)benzoyl, Compound D): which may be prepared following the procedure for Compound A.

Compound E

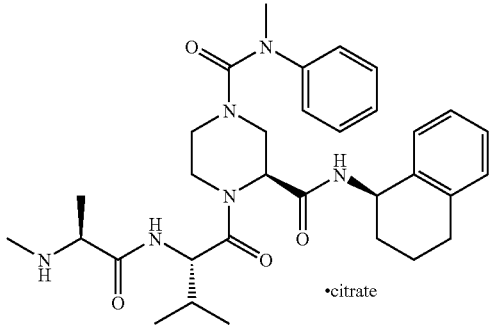

(S)-4-[(S)-3-Methyl-2-((S)-2-methylamino-propionylamino)-butyryl]-piperazine-1,3-dicarboxylic acid 1-(methyl-phenyl-amide) 3-{[(1R)-1,2,3,4-tetrahydro-naphthalen-1-yl)-amide]} (9, R=N-methyl-N-phenyl carbamoyl, Compound E): which may be prepared following the procedure for Compound A.

Compound F

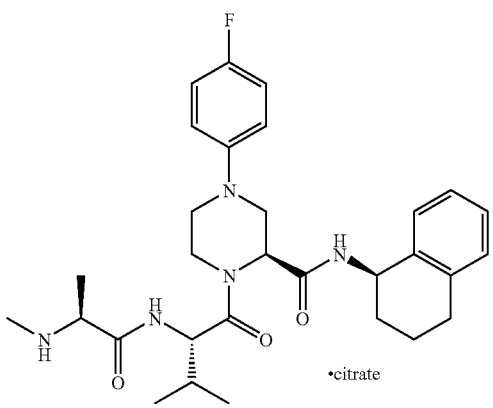

(S)-4-(4-Fluoro-phenyl)-1-[(S)-3-methyl-2-((S)-2-methylamino-propionylamino)butyryl]-piperazine-2-carboxylic acid [(1R)-1,2,3,4-tetrahydro-naphthalen-1-yl)]-amide (9, R=4-fluorophenyl, Compound F): which may be prepared following the procedure for Compound A.

Compound G

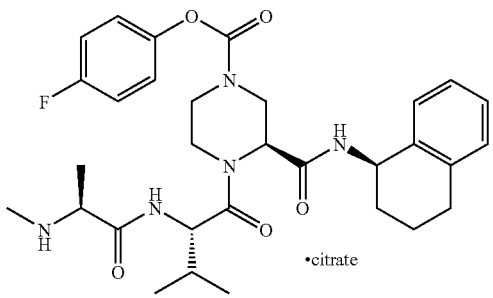

(S)-4-[(S)-3-Methyl-2-((S)-2-methylamino-propionylamino)-butyryl]-3-[(1R)-1,2,3,4-tetrahydro-naphthalen-1-ylcarbamoyl}-piperazine-1-carboxylic acid 4-fluoro-phenyl ester (9, R=4-fluorophenyloxycarbonyl, Compound G): which may be prepared following the procedure for Compound A.
Generally, compounds in Table A may be prepared from commonly available starting materials following the procedure for Series A.
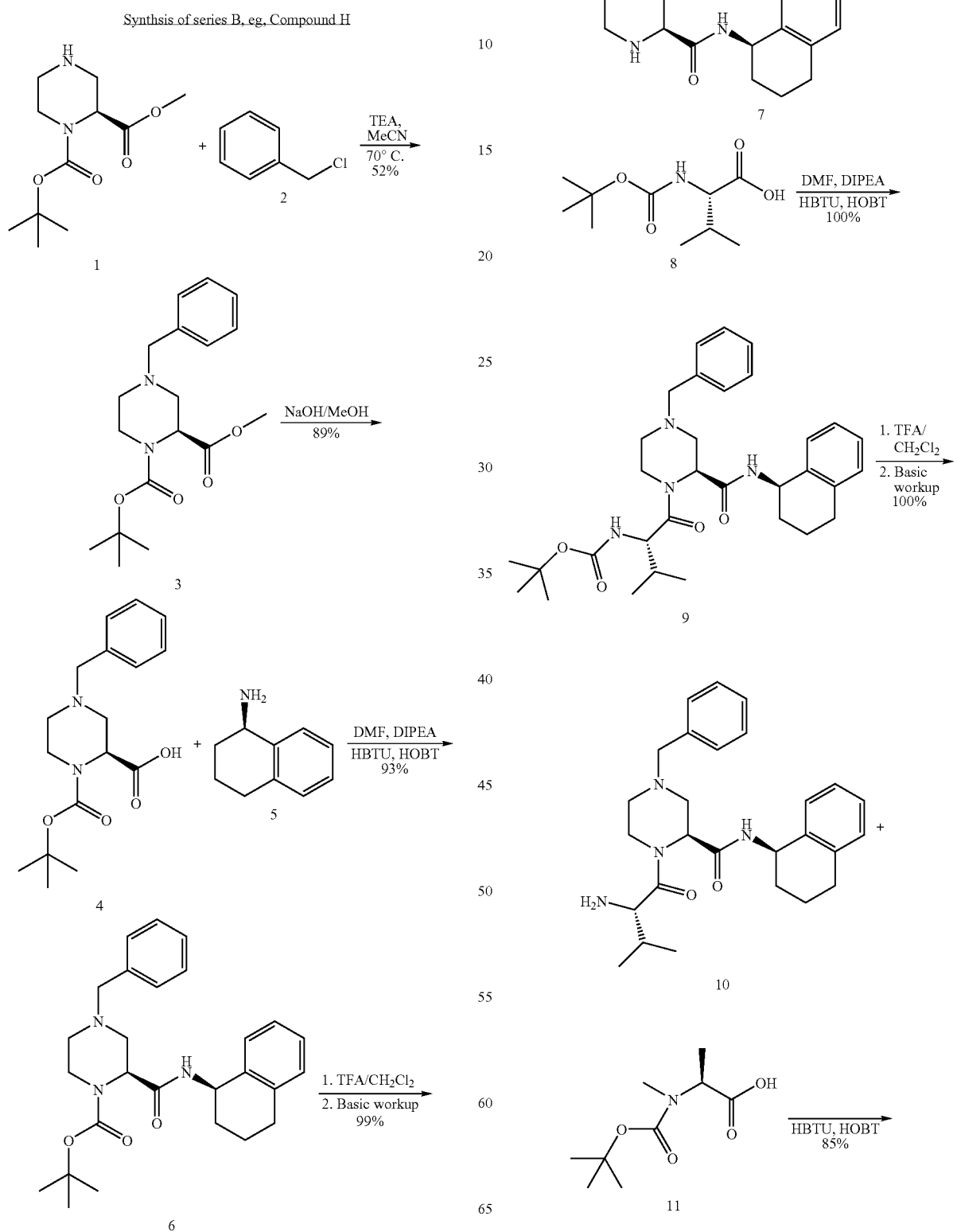

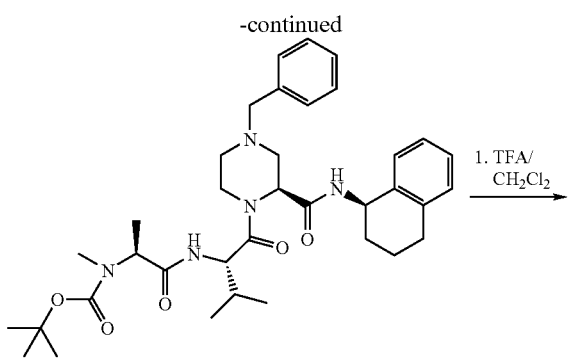

12

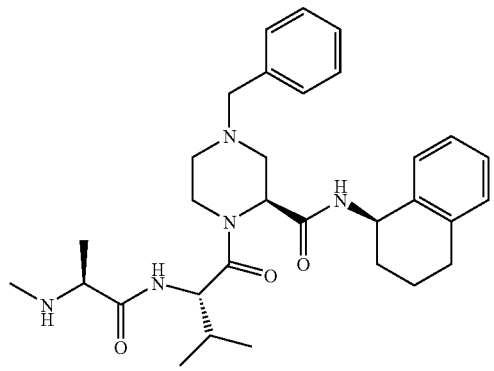

Compound H

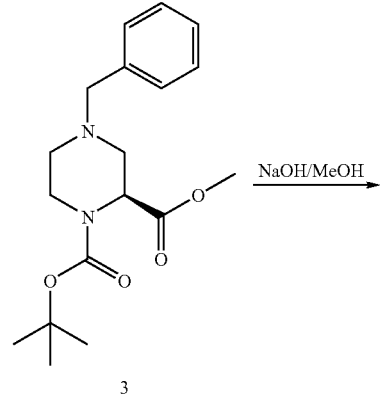

3

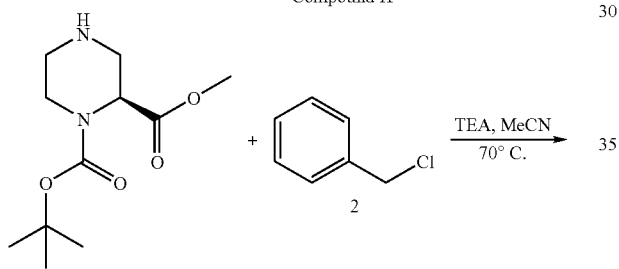

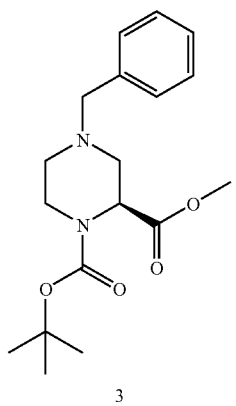

3

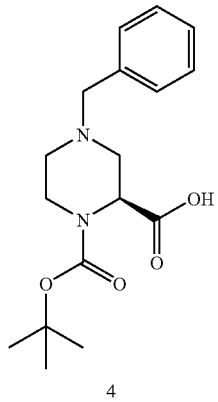

4

1. TFA/CH₂Cl₂

NaOH/MeOH

TEA, MeCN
70° C.

pressure. It is then diluted with dicholoromethane and washed with water and brine. The organic layer is dried over Na₂SO₄, filtered and concentrated under reduced pressure. The crude compound is flash column purified using hexane and ethylacetate gradient solvent system to yield 570 mg (52%) of the desired product.

Preferably, the water bath temperature is not raised more than 20° C., otherwise epimerization takes place.

(S)-4-Benzyl-piperazine-1,2-dicarboxylic acid 1-tert-butyl ester 2-methyl ester (3): To a dry 100.0 ml one necked round bottom flask equipped with a stirring bar is added (S)-1-N-Boc-piperazine-2-carboxylic methyl ester (800 mg, 3.275 mmol) under N₂. Anhydrous acetonitrile (20 ml) is added to the flask followed by benzyl chloride (0.38 ml, 3.275 mmol) and triethylamine (1.28 ml, 9.17 mmol). Condenser is then put on to the flask and the reaction mixture is heated at 71° C. for 20 minutes. The reaction mixture is allowed to come to room temperature and concentrated under reduced (S)-4-Benzyl-piperazine-1,2-dicarboxylic acid 1-tert-butyl ester (4): To the round bottom flask containing compound 3 (720 mg, 2.15 mmol) is added MeOH (20 ml) followed by 1 N NaOH (12.9 ml, 12.9 mmol) and stirred overnight at room temperature at which point LCMS shows product peak at 321 (M+H). The reaction mixture is concentrated under reduced pressure to remove methanol. Acidified to pH around three with acetic acid. The mixture is then extracted with DCM and the organic is washed with water twice and once with brine. The organic layer is dried over Na₂SO₄, filtered and concentrated under reduced pressure to get white solid 4 (615 mg, 89% yield). HPLC shows compound 4 to be greater than 98% pure.

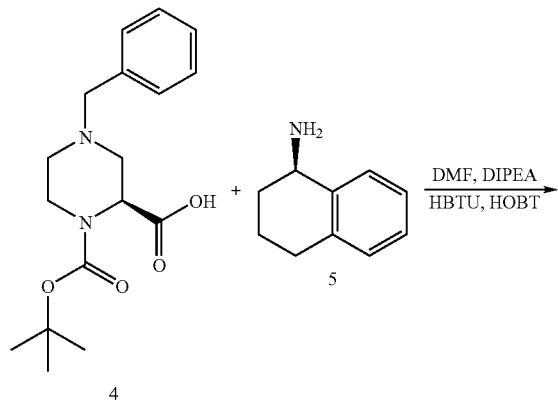

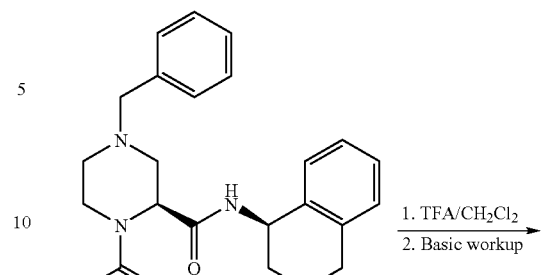

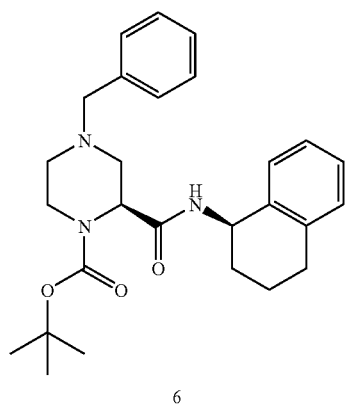

(S)-4-Benzyl-2-[(R)-(1,2,3,4-tetrahydro-naphthalen-1-yl) carbamoyl]-piperazine-1-carboxylic acid tert-butyl ester (6): Anhydrous DMF (20 ml) is added to a 100 ml round bottom flask containing compound 4 (325 mg, 1.014 mmol) under $N_2$. After ten minutes diisopropylamine (0.88 ml, 5.07 mmol) is added to the flask. It is then stirred at room temperature for 1.5 hrs. (R)-1,2,3,4-Tetrahydro-1-napthylamine (149.3 mg, 1.014 mmol) is then added to the flask and stirred for 1 hr. HBTU (423.07 mg, 1.115 mmol) is added to the reaction followed by HOBT (152.1 mg, 1.126 mmol). The reaction mixture is then stirred at room temperature under $N_2$ overnight at which point LCMS shows completion of the reaction. It is then diluted with EtOAc and washed subsequently with 1.0 M citric acid, brine, saturated sodiumbicarbonate, brine, water and brine. The organic layer is dried over $Na_2SO_4$, filtered and concentrated under reduced pressure. The crude compound is flash column purified using hexane and ethylacetate gradient solvent system to yield 423 mg (93%) of the desired product 6. HPLC shows this compound to be greater than 99% pure.

(S)-4-Benzyl-piperazine-2-carboxylic acid [(1R)-1,2,3,4-tetrahydro-naphthalen-1-yl]-amide (7) Dichloromethane (15 ml) is added to a 100 ml round bottom flask containing compound 6 (423 mg, 0.941 mmol) under $N_2$. TFA (3.84 ml, 49.86 mmol) is added to the flask and it is stirred overnight. Reaction mixture is concentrated under reduced pressure once the LCMS shows completion of the reaction. It is then diluted with DCM and basified to pH around 10 with saturated sodiumbicarbonate solution. Organic layer is washed with brine and dried over $Na_2SO_4$, filtered and concentrated under reduced pressure to get white foamed compound 7 (324 mg, 99% yield).

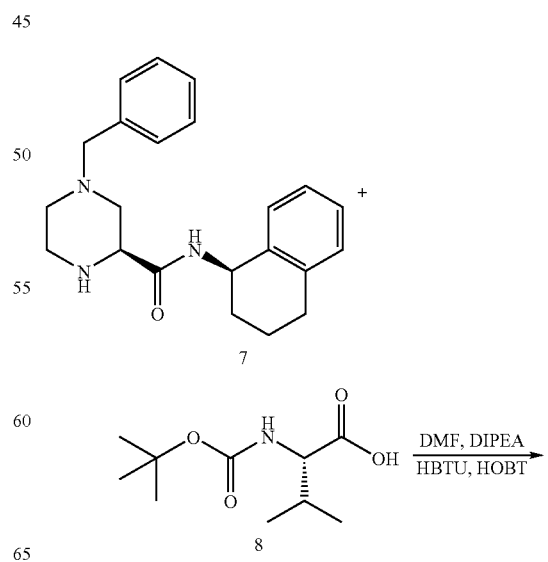

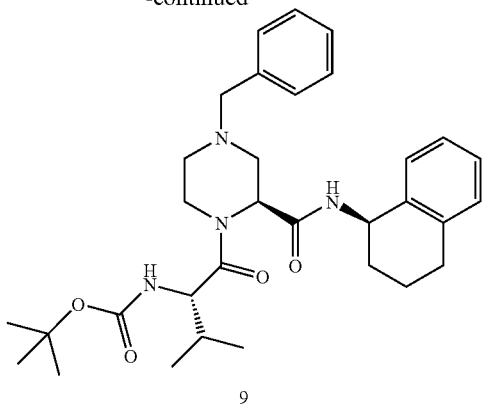

9

((S)-1-{(S)-4-Benzyl-2-[(R)-(1,2,3,4-tetrahydro-naphthalen-1-yl)carbamoyl]-piperazine-1-carbonyl}-2-methyl-propyl)-carbamic acid tert-butyl ester (9): Anhydrous DMF (11 ml) is added to a 100 ml round bottom flask containing compound 7 (190 mg, 0.544 mmol) under N₂. After ten minutes diisopropylamine (0.473 ml, 2.72 mmol) is added to the flask. It is then stirred at room temperature for 1 hr. Boc-L-valine (118.19 mg, 0.544 mmol) is then added to the flask and stirred for 1 hr. HBTU (227 mg, 0.598 mmol) is added to the reaction followed by HOBT (81.6 mg, 0.604 mmol). The reaction mixture is then stirred at room temperature under N₂ overnight at which point LCMS shows completion of the reaction. It is then diluted with EtOAc and washed subsequently with 1.0 M citric acid, brine, saturated sodiumbicarbonate, brine, water and brine. The organic layer is dried over Na₂SO₄, filtered and concentrated under reduced pressure to yield 356 mg (>100%) of the desired product 9.

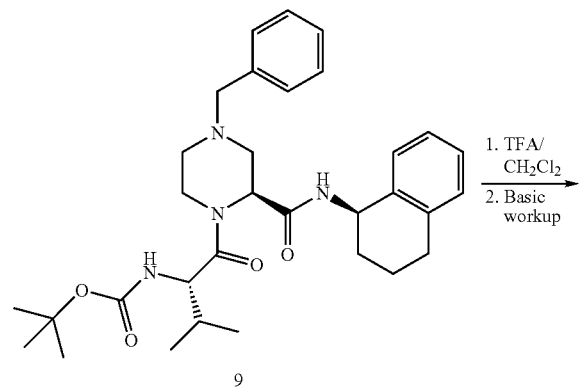

9

1. TFA/CH₂Cl₂
2. Basic workup

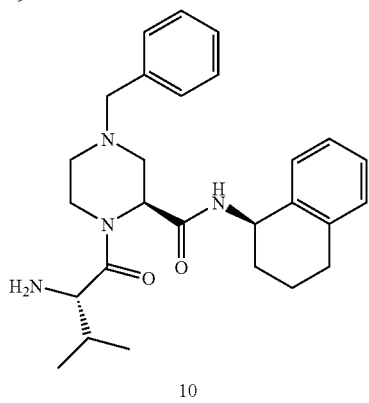

10

(S)-1-((S)-2-Amino-3-methyl-butyryl)-4-benzyl-piperazine-2-carboxylic acid [(1R)-1,2,3,4-tetrahydro-naphthalen-1-yl]-amide (10) Dichloromethane (10 ml) is added to a 100 ml round bottom flask containing compound 9 (300 mg, 0.547 mmol) under N₂. TFA (2.23 ml, 28.98 mmol) is added to the flask and it is stirred overnight. Reaction mixture is concentrated under reduced pressure once the LCMS shows completion of the reaction. It is then diluted with DCM and basified to pH around 10 with saturated sodiumbicarbonate solution. Organic layer is washed with brine and dried over Na₂SO₄, filtered and concentrated under reduced pressure to get white foamed compound 10 (250 mg, >100% yield). HPLC shows compound 10 to be 95% pure.

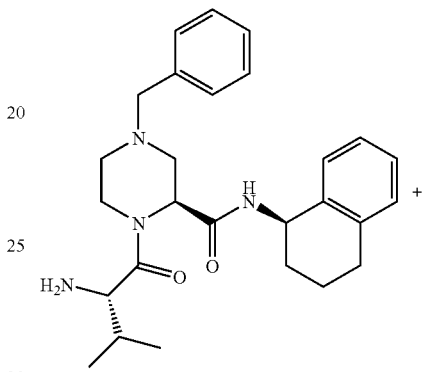

10

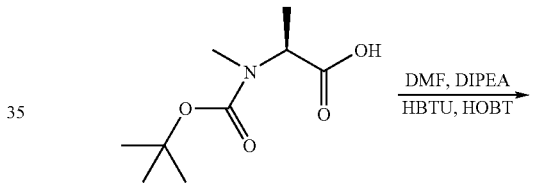

11

DMF, DIPEA
HBTU, HOBT

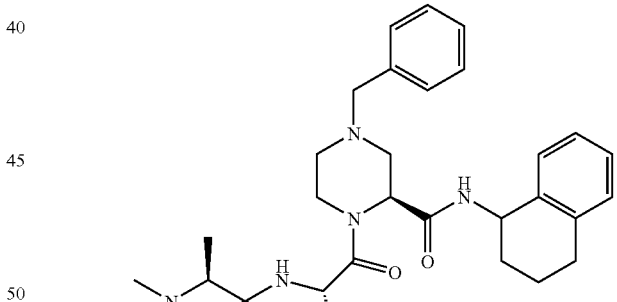

12

[(S)-1-((S)-1-{(S)-4-Benzyl-2-[(R)-(1,2,3,4-tetrahydro-naphthalen-1-yl)carb-amoyl]-piperazine-1-carbonyl}-2-methyl-propylcarbamoyl)-ethyl]-methyl-carbamic acid tert-butyl ester (12): nhydrous DMF (12 ml) is added to a 100 ml round bottom flask containing compound 10 (245 mg, 0.547 mmol) under N₂. After ten minutes diisopropylamine (0.476 ml, 2.735 mmol) is added to the flask. It is then stirred at room temperature for 1 hr. Boc-N-methyl-L-alanine (111.17 mg, 0.547 mmol) is then added to the flask and stirred for another 1 hr. HBTU (228.22 mg, 0.602 mmol) is added to the reaction followed by HOBT (82.05 mg, 0.607 mmol). The reaction mixture is then stirred at room temperature under $N_2$ overnight at which point LCMS shows completion of the reaction. It is then diluted with EtOAc and washed subsequently with 1.0 M citric acid, brine, saturated sodium bicarbonate, brine, water and brine. The organic layer is dried over $Na_2SO_4$, filtered and concentrated under reduced pressure. The crude compound is flash column purified using hexane and ethylacetate gradient solvent system to yield white foamy 294 mg (85%) of the desired product 12.

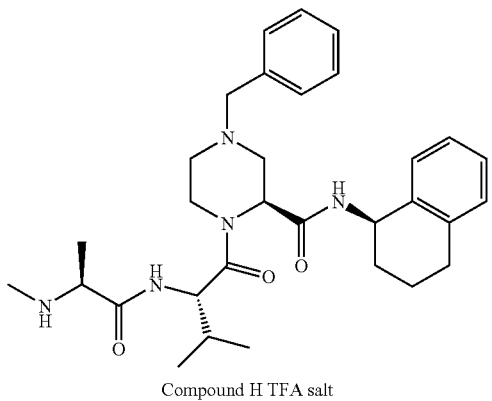

12

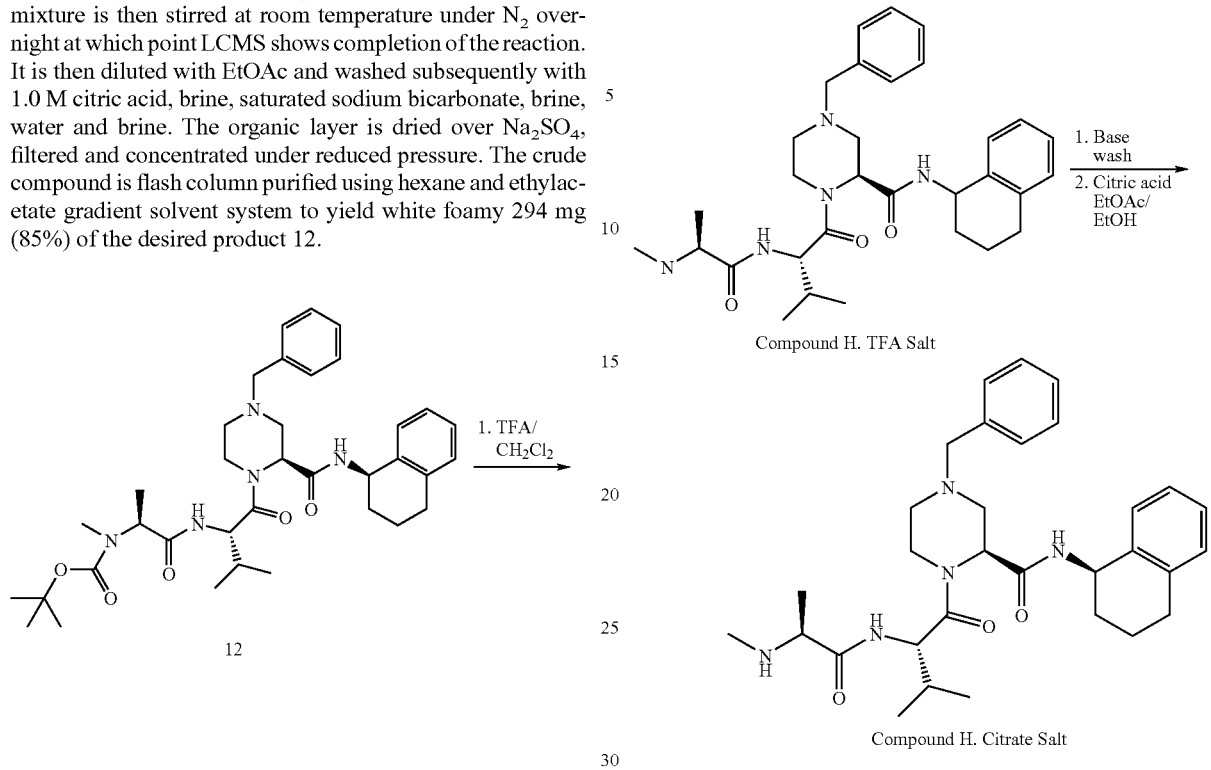

Compound H. TFA Salt

Compound H. Citrate Salt

Compound H TFA salt (S)-4-Benzyl-1-[(S)-3-methyl-2-((S)-2-methylamino-propionylamino)-butyryl]-piperazine-2-carboxylic acid [(1R)-1,2,3,4-tetrahydro-naphthalen-1-yl]-amide Dichloromethane (9.0 ml) is added to a 100 ml round bottom flask containing compound 12 (294 mg, 0.464 mmol) under $N_2$. TFA (1.89 ml, 24.58 mmol) is added to the flask and it is stirred overnight. Reaction mixture is concentrated under reduced pressure once the LCMS shows completion of the reaction. It is concentrated under reduced pressure. It is further co-evaporated with hexane and ether to get off-white solid. This crude compound is HPLC purified using acetonitrile and 0.1% TFA in water solvent system to get the final compound, example 1 (290 mg, 96.5%). HPLC shows this compound to be greater than 99% pure.

Example 1-TFA salt (216 mg, 0.33 mmol) is dissolved in EtOAc and washed with saturated sodiumbicarbonate solution twice. The pH of aqueous layer is around 10. Organic layer is washed with brine and dried over $Na_2SO_4$, filtered and concentrated under reduced pressure. It is further dried on high vacuum to get white foam with quantitative yield. It is then re-dissolved in EtOAc (10 ml) and EtOH (0.2 ml). Anhydrous citric acid sold (59 mg, 0.31 mmol) is added to the flask and stirred under $N_2$ for one hr. The reaction mixture is concentrated under reduced pressure to get white solid. It is dried under high vacuum (225 mg, 94%).

Pharmaceutical Compositions

The present invention further includes pharmaceutical compositions comprising a pharmaceutically effective amount of one or more of the above-described compounds as active ingredient. Pharmaceutical compositions according to the invention are suitable for enteral, such as oral or rectal, and parenteral administration to mammals, including man, for the treatment of proliferative diseases, including tumors, especially cancerous tumors, and other cancers alone or in combination with one or more pharmaceutically acceptable carriers.

The inventive compounds are useful for the manufacture of pharmaceutical compositions having an effective amount the compound in conjunction or admixture with excipients or carriers suitable for either enteral or parenteral application. Examples include tablets and gelatin capsules comprising the active ingredient together with (a) diluents; (b) lubricants, (c) binders (tablets); if desired, (d) disintegrants; and/or (e) absorbents, colorants, flavors and sweeteners. Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. The compositions are prepared according to conventional mixing, granulating or coating methods, respectively, and contain preferably about 1 to 50% of the active ingredient.

More generally, the present invention also relates to the use of the compounds of the invention for the manufacture of a medicament, in particular for the manufacture of a medicament for the treatment of proliferative diseases.

Also contemplated is the use of the pharmaceutical compositions described hereinbefore and hereinafter for the treatment of a proliferative disease.

Suitable formulations also include formulations for parenteral administration such as aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use.

Extemporaneous injection solutions and suspensions may be prepared from sterile powders, granules and tablets of the kind previously described.

The pharmaceutical composition contains a pharmaceutically effective amount of the present active agent along with other pharmaceutically acceptable exicipients, carriers, fillers, diluents and the like. The term therapeutically effective amount as used herein indicates an amount necessary to administer to a host to achieve a therapeutic result, especially an anti-tumor effect, e.g., inhibition of proliferation of malignant cancer cells, benign tumor cells or other proliferative cells.

As discussed above, the compounds of the present invention are useful for treating proliferative diseases. Thus, the present invention further relates to a method of treating a proliferative disease which comprises administering a therapeutically effective amount of a compound of the invention to a mammal, preferably a human, in need of such treatment.

A proliferative disease is mainly a tumor disease (or cancer) (and/or any metastases).

The inventive compounds are particularly useful for treating a tumor which is a breast cancer, genitourinary cancer, lung cancer, gastrointestinal cancer, epidermoid cancer, melanoma, ovarian cancer, pancreas cancer, neuroblastoma, head and/or neck cancer or bladder cancer, or in a broader sense renal, brain or gastric cancer; in particular (i) a breast tumor; an epidermoid tumor, such as an epidermoid head and/or neck tumor or a mouth tumor; a lung tumor, for example a small cell or non-small cell lung tumor; al gastrointestinal tumor, for example, a colorectal tumor; or a genitourinary tumor, for example, a prostate tumor (especially a hormone-refractory prostate tumor); or (ii) a proliferative disease that is refractory to the treatment with other chemotherapeutics; or (iii) a tumor that is refractory to treatment with other chemotherapeutics due to multidrug resistance. In a broader sense of the invention, a proliferative disease may furthermore be a hyperproliferative condition such as leukemias, hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

Where a tumor, a tumor disease, a carcinoma or a cancer are mentioned, also metastasis in the original organ or tissue and/or in any other location are implied alternatively or in addition, whatever the location of the tumor and/or metastasis.

The inventive compound is selectively toxic or more toxic to rapidly proliferating cells than to normal cells, particularly in human cancer cells, e.g., cancerous tumors, the compound has significant antiproliferative effects and promotes differentiation, e.g., cell cycle arrest and apoptosis.

The compounds of the present invention may be administered alone or in combination with other anticancer agents, such as compounds that inhibit tumor angiogenesis, for example, the protease inhibitors, epidermal growth factor receptor kinase inhibitors, vascular endothelial growth factor receptor kinase inhibitors and the like; cytotoxic drugs, such as antimetabolites, like purine and pyrimidine analog antimetabolites; antimitotic agents like microtubule stabilizing drugs and antimitotic alkaloids; platinum coordination complexes; anti-tumor antibiotics; alkylating agents, such as nitrogen mustards and nitrosoureas; endocrine agents, such as adrenocorticosteroids, androgens, anti-androgens, estrogens, anti-estrogens, aromatase inhibitors, gonadotropin-releasing hormone agonists and somatostatin analogues and compounds that target an enzyme or receptor that is overexpressed and/or otherwise involved a specific metabolic pathway that is unregulated in the tumor cell, for example ATP and GTP phosphodiesterase inhibitors, histone deacetylase inhibitors, protein kinase inhibitors, such as serine, threonine and tyrosine kinase inhibitors, for example, Abelson protein tryosine kinase and the various growth factors, their receptors and kinase inhibitors therefore, such as, epidermal growth factor receptor kinase inhibitors, vascular endothetial growth factor I receptor kinase inhibitors, fibroblast growth factor inhibitors, insulin-like growth factor receptor inhibitors and platelet-derived growth factor receptor kinase inhibitors and the like; methionine aminopeptidase inhibitors, proteasome inhibitors, and cyclooxygenase inhibitors, for example, cyclooxygenase-1 or -2 inhibitors.

The present invention further relates to a method of promoting apoptosis in rapidly proliferating cells, wherein the method comprises contacting the rapidly proliferating cells with an effective apoptosis promoting amount of an inhibitor of IAP (IAPI). Preferably, the IAPI compound is a compound of present formula I.

EXAMPLES

Example 1

The following compounds are produced by methods described in literature, and verified by HPLC-MS.

TABLE 1

| # | IUPAC | HPLC-MS MS (ESI) |
|---|---|---|
| 1 | 4-ethyl-1-[3-methyl-2-(2methylaminopropionyl-amino)-butyryl]-piperazine-2-carboxylic acid-(1,2,3,4-tetrahydro-naphthalin-1-yl)-amide | 472.45 $(M + H)^+$ |
| 2 | 4-isopropyl-1-[3-methyl-2-(2-methylaminopropionylamino)-butyryl]-piperazine-2-carboxylic acid-(1,2,3,4-tetrahydro-naphthalin-1-yl)-amide | 486.41 $(M + H)^+$ |
| 3 | 4-cyclohexyl-1-[3-methyl-2-(2-methylaminopropionyl-amino)-butyryl]-piperazine-2-carboxylic acid-(1,2,3,4-tetrahydro-naphthalin-1-yl)-amide | 526.44 $(M + H)^+$ |
| 4 | 1-[3,3-dimethyl-2-(2-methylaminopropionyl-amino)butyryl]-4-phenylpiperazine-2-carboxylic acid-(1,2,3,4-tetrahydro-naphthalin-1-yl)-amide | 534.43 $(M + H)^+$ |
| 5 | 1-[3,3-dimethyl-2-(2-methylaminopropionyl-amino)butyryl]-4-(5-nitropyridin-2-yl)-piperazine-2-carboxylic acid-(1,2,3,4-tetrahydronaphthalin-1-yl)-amide | 580.40 $(M + H)^+$ |
| 6 | 5-[4-[3-methyl-2-(2-methylaminopropionylamino)-butyryl]-3-(1,2,3,4-tetrahydronaphthalin-1-ylcarbamoyl)-piperazin-1-yl]-naphthalene-1-sulfonic acid | 650.39 $(M + H)^+$ |
| 7 | 4-benzyl-1-[3,3-dimethyl-2-(2-methylaminopropionyl-amino)-butyryl]-piperazine-2-carboxylic acid-(1,2,3,4-tetrahydro-naphthalin-1-yl)-amide | 548.6 $(M + H)^+$ |
| 8 | 4-cyclohexyl-1-[3-methyl-2-(2-methylaminopropionyl-amino)-butyryl]-1,4,5,6-tetrahydropyrazine-2-carboxylic acid-(1,2,3,4-tetrahydro-naphthalin-1-yl)-amide | 524.5 $(M + H)^+$ |
| 9 | 4-cyclohexyl-1-[3-methyl-2-(2-methylaminopropionyl-amino)-butyryl]-4,5,6,7-tetrahydro-1H-[1,4]-diazepine-2-carboxylic acid-(1,2,3,4-tetrahydro-naphthalin-1-yl)-amide | 538.5 $(M + H)^+$ |
| 10 | 3-chloro-4-cyclohexyl-1-[3-methyl-2-(2-methylamino-propionylamino)-butyryl]-[1,4]-diazepan-2-carboxylic acid-(1,2,3,4-tetrahydronaphthalin-1-yl)-amide | 574.5, 576.5 $(M + H)^+$ |
| 11 | 1-[2-(3-aminomethylazetidin-1-yl)-acetyl]-4-benzyl-piperazine-2-carboxylic acid-(1,2,3,4-tetrahydronaphthalin-1-yl)-amide | 476.4 $(M + H)^+$ |
| 12 | 1-[2-(3-aminomethylazetidin-1-yl)-acetyl]-4-benzyl-1,4,5,6-tetrahydropyrazine-2-carboxylic acid-(1,2,3,4-tetrahydro-naphthalin-1-yl)-amide | 474.4 $(M + H)^+$ |

Example 2

Assays

Cell Proliferation Assay

The ability of compounds of the invention to inhibit tumor cell growth in vitro is monitored using the CellTiter 96® AQ$_{ueous}$ Non-Radioactive Cell Proliferation Assay (Promega). This assay is composed of solutions of a novel tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine methosulfate) PMS. MTS is bioreduced by cells into a formazan product, the absorbance of which is measured at 490 nm. The conversion of MTS into the aqueous soluble formazan product is accomplished by dehydrogenase enzymes found in metabolically active cells. The quantity of formazan product as measured by the amount of 490 nm absorbance is directly proportional to the number of living cells in culture. The IC$_{50}$ values of compounds listed in Tables 1-3 in the described cell assay range from <0.01 nM to >10 μM. Values for preferred compounds range from 0.005-10 μM.

In order to measure the ability of the inventive compounds to bind the BIR3 peptide binding pocket, a solution phase assay on the FMAT or ELISA technology platform is utilized.

Fmat

Biotinylated Smac 7-mer peptide (AVPIAQK, lysine ε-amino group is biotinylated) is immobilized on streptavidin coated beads. GST-BIR3 fusion protein is precipitated with FMAT beads and is detected using fluorescent tagged anti-GST antibodies. Importantly, non-biotinylated Smac peptide is highly effective at competing GST-BIR3 off the FMAT beads. The IC50 for non-biotinylated Smac is 400 nM. The IC50 values of compounds listed in Tables 1-3 in the described FMAT assay range from 0.025 to greater than 10 μM.

Elisa

Compounds are incubated with GST-BIR3 fusion protein and biotinylated SMAC peptide (AVPFAQK) in stretavidin-coated 96 well plates. For XIAP BIR3Smac Elisa, a GST-BIR3 fusion containing amino acids 248-358 from XIAP was used. For CIAP1 BIR3 Smac Elisa, a GST-BIR3 fusion containing amino acids 259-364 from CIAP1 was used. Following a 30 minute incubation, wells are extensively washed. The remaining GST-BIR3 fusion protein is monitored by ELISA assay involving first, incubation with goat anti-GST antibodies followed by washing and incubation with alkaline phosphatase conjugated anti-goat antibodies. Signal is amplified using Attophos (Promega) and read with Cytoflour Ex 450 nm/40 and Em 580 nm. IC50s correspond to concentration of compound which displaces half of GST-BIR3 signal. The IC50 for non-biotinylated Smac is 400 nM. The IC50 values of compounds listed in Tables 1-3 in the described ELISA assays range from 0.005 μM to greater than 10 μM.

Example 3

IC50 values for Series A compounds for XIAP. An assay capable of measuring disruption of the Smac peptide-(XIAP) BIR3 protein-protein interaction is established in the art as described in Example 2. In this assay IAP Inhibitor compounds compete with an immobilized Smac peptide for occupancy of the BIR3 binding pocket of XIAP. The rationale for this strategy results from the mutually exclusive nature of either Caspase 9 or Smac binding to the BIR3 pocket.

Assays are performed and IC50 values are calculated as follows:

$IC_{50}$ calculations input 3×4 µL stopped assay on Immobilon membrane, not washed background (3 wells) assay with $H_2O$ instead of enzyme positive control (4 wells) 3% DMSO instead of compound bath control (1 well) no reaction mix $IC_{50}$ values are calculated by logarithmic regression analysis of the percentage inhibition of each compound at 4 concentrations (usually 3- or 10-fold dilution series starting at 10 µM). In each experiment, the actual inhibition by reference compound is used for normalization of $IC_{50}$ values to the basis of an average value of the reference inhibitor:

Normalized $IC_{50}$=measured $IC_{50}$ average ref. $IC_{50}$/measured ref. $IC_{50}$ Activity determinations of compounds herein using the testing method described herein and as are well known in the art, are used with the following test compounds of formula (I). As shown in Table 2, Series A test compounds exhibit activity against XIAP. "Activity" as used herein is defined as having $IC_{50}$ values for IAP target inhibition of less than 10 µM. Specifically, in the table:

TABLE 2

$IC_{50}$ Levels for Series A compounds

| # | IUPAC | XIAP $IC_{50}$ |
|---|---|---|
| 1 | 4-Benzyl-1-[3-methyl-2-(2-methylamino-propionylamino)-butyryl]-piperazine-2-carboxylic acid (1,2,3,4-tetrahydro-naphthalen-1-yl)-amide | X |
| 2 | 4-Benzenesulfonyl-1-[3-methyl-2-(2-methylamino-propionylamino)-butyryl]-piperazine-2-carboxylic acid (1,2,3,4-tetrahydro-naphthalen-1-yl)-amide | X |
| 3 | (S)-1-[(S)-3-Methyl-2-((S)-2-methylamino-propionylamino)-butyryl]-4-pyridin-3-ylmethyl-piperazine-2-carboxylic acid (1,2,3,4-tetrahydro-naphthalen-1-yl)-amide | X |
| 4 | (S)-1-[(S)-3-Methyl-2-((S)-2-methylamino-propionylamino)-butyryl]-4-(3-phenoxy-benzyl)-piperazine-2-carboxylic acid (1,2,3,4-tetrahydro-naphthalen-1-yl)-amide | X |
| 5 | (S)-4-[(S)-3-Methyl-2-((S)-2-methylamino-propionylamino)-butyryl]-piperazine-1,3-dicarboxylic acid 1-benzylamide 3-[(1,2,3,4-tetrahydro-naphthalen-1-yl)-amide] | X |
| 6 | (S)-4-(4-Methoxy-benzyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 7 | (S)-4-Cyclopentylmethyl-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 8 | (S)-4-Isobutyl-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 9 | (S)-1-[(S)-3-Methyl-2-((S)-2-methylamino-propionylamino)-butyryl]-4-pyridin-4-ylmethyl-piperazine-2-carboxylic acid (1,2,3,4-tetrahydro-naphthalen-1-yl)-amide | X |
| 10 | (S)-4-(4-Fluoro-benzyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 11 | (S)-4-Cyclohexanesulfonyl-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 12 | (S)-1-[(S)-3-Methyl-2-((S)-2-methylamino-propionylamino)-butyryl]-4-(4-trifluoromethyl-benzyl)-piperazine-2-carboxylic acid (1,2,3,4-tetrahydro-naphthalen-1-yl)-amide | X |
| 13 | (S)-4-[(S)-3-Methyl-2-((S)-2-methylamino-propionylamino)-butyryl]-3-(1,2,3,4-tetrahydro-naphthalen-1-ylcarbamoyl)-piperazine-1-carboxylic acid benzyl ester | X |
| 14 | (S)-4-Benzyl-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 15 | (S)-4-(1H-Indol-4-ylmethyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 16 | (S)-4-(4-Acetylamino-benzyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 17 | (S)-4-(4-Fluoro-benzoyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 18 | (S)-4-(3-Methoxy-propionyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 19 | (S)-4-Cyclohexylmethyl-1-[(S)-3-methyl-2-((S)-2-methylamino-propionylamino)-butyryl]-piperazine-2-carboxylic acid (1,2,3,4-tetrahydro-naphthalen-1-yl)-amide | X |

TABLE 2-continued

IC$_{50}$ Levels for Series A compounds

| # | IUPAC | XIAP IC$_{50}$ |
|---|---|---|
| 20 | (S)-1-[(S)-3-Methyl-2-((S)-2-methylamino-propionylamino)-butyryl]-4-(3,3,3-trifluoro-propyl)-piperazine-2-carboxylic acid (1,2,3,4-tetrahydro-naphthalen-1-yl)-amide | X |
| 21 | (S)-4-(3,3-Dimethyl-butyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 22 | (S)-1-[(S)-3-Methyl-2-((S)-2-methylamino-propionylamino)-butyryl]-4-thiazol-5-ylmethyl-piperazine-2-carboxylic acid (1,2,3,4-tetrahydro-naphthalen-1-yl)-amide | X |
| 23 | (S)-1-[(S)-3-Methyl-2-((S)-2-methylamino-propionylamino)-butyryl]-4-(4-trifluoromethoxy-benzyl)-piperazine-2-carboxylic acid (1,2,3,4-tetrahydro-naphthalen-1-yl)-amide | X |
| 24 | (S)-4-(3-Methyl-butyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 25 | (S)-1-[(S)-3-Methyl-2-((S)-2-methylamino-propionylamino)-butyryl]-4-propyl-piperazine-2-carboxylic acid (1,2,3,4-tetrahydro-naphthalen-1-yl)-amide | X |
| 26 | (S)-1-[(S)-3-Methyl-2-((S)-2-methylamino-propionylamino)-butyryl]-4-(3,3,3-trifluoro-propane-1-sulfonyl)-piperazine-2-carboxylic acid (1,2,3,4-tetrahydro-naphthalen-1-yl)-amide | X |
| 27 | (S)-4-(4-Acetylamino-benzoyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 28 | (S)-4-[(S)-3-Methyl-2-((S)-2-methylamino-propionylamino)-butyryl]-piperazine-1,3-dicarboxylic acid 1-cyclopentylamide 3-[(1,2,3,4-tetrahydro-naphthalen-1-yl)-amide] | X |
| 29 | (S)-4-(3-Methoxy-benzyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 30 | (S)-4-Methanesulfonyl-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 31 | (S)-4-[(S)-3-Methyl-2-((S)-2-methylamino-propionylamino)-butyryl]-3-(1,2,3,4-tetrahydro-naphthalen-1-ylcarbamoyl)-piperazine-1-carboxylic acid isobutyl ester | X |
| 32 | (S)-4-Ethyl-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 33 | (S)-4-Butyl-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 34 | (S)-4-[(S)-3-Methyl-2-((S)-2-methylamino-propionylamino)-butyryl]-3-(1,2,3,4-tetrahydro-naphthalen-1-ylcarbamoyl)-piperazine-1-carboxylic acid 4-fluoro-phenyl ester | X |
| 35 | (S)-4-(4-Fluoro-benzenesulfonyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 36 | (S)-4-Cyclopropylmethyl-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 37 | (S)-4-(2-Methoxy-benzyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 38 | (S)-4-(2-Methoxy-ethyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 39 | (S)-4-[(S)-3-Methyl-2-((S)-2-methylamino-propionylamino)-butyryl]-piperazine-1,3-dicarboxylic acid 1-tert-butylamide 3-[(1,2,3,4-tetrahydro-naphthalen-1-yl)-amide] | X |
| 40 | (S)-4-[(S)-3-Methyl-2-((S)-2-methylamino-propionylamino)-butyryl]-piperazine-1,3-dicarboxylic acid 1-[(4-fluoro-phenyl)-amide] 3-[(1,2,3,4-tetrahydro-naphthalen-1-yl)-amide] | X |
| 41 | (S)-4-[(S)-3-Methyl-2-((S)-2-methylamino-propionylamino)-butyryl]-piperazine-1,3-dicarboxylic acid 1-phenylamide 3-[(1,2,3,4-tetrahydro-naphthalen-1-yl)-amide] | X |
| 42 | (S)-4-(3-Isoxazol-5-yl-thiophene-2-sulfonyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 43 | (S)-4-(4-Cyano-benzyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 44 | (S)-4-(4-Fluoro-phenyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 45 | (S)-4-(2-Chloro-benzyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |

TABLE 2-continued

IC$_{50}$ Levels for Series A compounds

| # | IUPAC | XIAP IC$_{50}$ |
|---|---|---|
| 46 | (S)-1-[(S)-3-Methyl-2-((S)-2-methylamino-propionylamino)-butyryl]-4-phenethyl-piperazine-2-carboxylic acid (1,2,3,4-tetrahydro-naphthalen-1-yl)-amide | X |
| 47 | (S)-1-[(S)-3-Methyl-2-((S)-2-methylamino-propionylamino)-butyryl]-4-(pyrrolidine-1-carbonyl)-piperazine-2-carboxylic acid (1,2,3,4-tetrahydro-naphthalen-1-yl)-amide | X |
| 48 | (S)-4-[(S)-3-Methyl-2-((S)-2-methylamino-propionylamino)-butyryl]-piperazine-1,3-dicarboxylic acid 1-isopropylamide 3-[(1,2,3,4-tetrahydro-naphthalen-1-yl)-amide] | X |
| 49 | (S)-1-[(S)-3-Methyl-2-((S)-2-methylamino-propionylamino)-butyryl]-4-pyridin-2-ylmethyl-piperazine-2-carboxylic acid (1,2,3,4-tetrahydro-naphthalen-1-yl)-amide | X |
| 50 | (S)-4-[(S)-3-Methyl-2-((S)-2-methylamino-propionylamino)-butyryl]-piperazine-1,3-dicarboxylic acid 1-(methyl-phenyl-amide) 3-[(1,2,3,4-tetrahydro-naphthalen-1-yl)-amide] | X |
| 51 | (S)-4-(4-Methyl-benzyl)-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 52 | (S)-4-Benzyl-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 53 | (S)-4-Benzyl-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 54 | (S)-4-Benzyl-1-[(S)-3-methyl-2-((S)-2-methylamino-propionylamino)-butyryl]-piperazine-2-carboxylic acid (1,2,3,4-tetrahydro-naphthalen-1-yl)-amide | X |
| 55 | (S)-4-Benzyl-1-[(S)-2-cyclohexyl-2-((S)-2-methylamino-propionylamino)-acetyl]-piperazine-2-carboxylic acid (1,2,3,4-tetrahydro-naphthalen-1-yl)-amide | X |
| 56 | (S)-1-[(S)-3-Methyl-2-((S)-2-methylamino-propionylamino)-butyryl]-piperazine-2-carboxylic acid (1,2,3,4-tetrahydro-naphthalen-1-yl)-amide | X |
| 57 | [(S)-1-((S)-1-{(S)-4-Benzyl-2-[(R)-(1,2,3,4-tetrahydro-naphthalen-1-yl)carbamoyl]-piperazine-1-carbonyl}-2-methyl-propylcarbamoyl)-ethyl]-methyl-carbamic acid tert-butyl ester | — |
| 58 | [(S)-1-((S)-2-{(S)-4-Benzyl-2-[(R)-(1,2,3,4-tetrahydro-naphthalen-1-yl)carbamoyl]-piperazin-1-yl}-1-cyclohexyl-2-oxo-ethylcarbamoyl)-ethyl]-methyl-carbamic acid tert-butyl ester | — |
| 59 | (S)-1-[(S)-2-Cyclohexyl-2-((S)-2-methylamino-propionylamino)-acetyl]-piperazine-2-carboxylic acid (1,2,3,4-tetrahydro-naphthalen-1-yl)-amide | X |

"X" indicates an IC$_{50}$ value of less than 10 μM for XIAP.
"-" indicates an IC$_{50}$ value of equal or greater than 10 μM for XIAP.

Example 4

IC50 values for Series B compounds are provided for XIAP. Assays are performed as described above using methods well known in the art.

Activity determinations of compounds herein using the testing method described herein and as are well known in the art, are used with the following test compounds of formula (I). As shown in Table 3, Series B test compounds exhibit activity against XIAP. "Activity" as used herein is defined as having IC$_{50}$ values for IAP target inhibition of less than 10 μM. Specifically, in the table:

TABLE 3

IC$_{50}$ Levels for Series B compounds

| # | IUPAC | XIXP IC$_{50}$ |
|---|---|---|
| 61 | (S)-4-Benzyl-1-[(S)-3-methyl-2-((S)-2-methylamino-propionylamino)-butyryl]-piperazine-2-carboxylic acid phenethyl-amide | X |
| 62 | (S)-4-Benzyl-1-[(S)-3-methyl-2-((S)-2-methylamino-propionylamino)-butyryi]-piperazine-2-carboxylic acid indan-1-ylamide | X |
| 63 | (S)-4-Benzyl-1-[(S)-3-methyl-2-((S)-2-methylamino-propionylamino)-butyryl]-piperazine-2-carboxylic acid [2-(3-fluoro-phenyl)-ethyl]-amide | X |

TABLE 3-continued

IC$_{50}$ Levels for Series B compounds

| # | IUPAC | XIXP IC$_{50}$ |
|---|---|---|
| 64 | (S)-4-Benzyl-1-[(S)-3-methyl-2-((S)-2-methylamino-propionylamino)-butyryl]-piperazine-2-carboxylic acid benzhydryl-amide | X |
| 65 | (S)-4-Benzyl-1-[(S)-3-methyl-2-((S)-2-methylamino-propionylamino)-butyryl]-piperazine-2-carboxylic acid benzylamide | X |
| 66 | (S)-4-Benzyl-1-[(S)-3-methyl-2-((S)-2-methylamino-propionylamino)-butyryl]-piperazine-2-carboxylic acid (2-pyridin-3-yl-ethyl)-amide | — |
| 67 | (S)-4-Benzyl-1-[(S)-3-methyl-2-((S)-2-methylamino-propionylamino)-butyryl]-piperazine-2-carboxylic acid [2-(2-fluoro-phenyl)-ethyl]-amide | X |
| 68 | (S)-4-Benzyl-1-[(S)-3-methyl-2-((S)-2-methylamino-propionylamino)-butyryl]-piperazine-2-carboxylic acid (1,2,3,4-tetrahydro-naphthalen-2-yl)-amide | X |
| 69 | (S)-4-Benzyl-1-[(S)-3-methyl-2-((S)-2-methylamino-propionylamino)-butyryl]-piperazine-2-carboxylic acid (2-pyridin-4-yl-ethyl)-amide | — |
| 70 | (S)-4-Benzyl-1-[(S)-3-methyl-2-((S)-2-methylamino-propionylamino)-butyryl]-piperazine-2-carboxylic acid 4-fluoro-benzylamide | X |
| 71 | (S)-4-Benzyl-1-[(S)-3-methyl-2-((S)-2-methylamino-propionylamino)-butyryl]-piperazine-2-carboxylic acid [2-(4-fluoro-phenyl)-ethyl]-amide | X |
| 72 | (S)-4-Benzyl-1-[(S)-3-methyl-2-((S)-2-methylamino-propionylamino)-butyryl]-piperazine-2-carboxylic acid (3-phenyl-propyl)-amide | — |
| 73 | (S)-4-Benzyl-1-[(S)-3-methyl-2-((S)-2-methylamino-propionylamino)-butyryl]-piperazine-2-carboxylic acid (thiazol-2-ylmethyl)-amide | — |
| 74 | (S)-4-Benzyl-1-[(S)-3-methyl-2-((S)-2-methylamino-propionylamino)-butyryl]-piperazine-2-carboxylic acid (1,2,3,4-tetrahydro-naphthalen-2-yl)-amide | X |
| 75 | (S)-4-Benzyl-1-[(S)-3-methyl-2-((S)-2-methylamino-propionylamino)-butyryl]-piperazine-2-carboxylic acid (9H-fluoren-9-yl)-amide | X |
| 76 | (S)-4-Benzyl-1-[(S)-3-methyl-2-((S)-2-methylamino-propionylamino)-butyrl]-piperazine-2-carboxylic acid ethyl-(1,2,3,4-tetrahydro-naphthalen-1-yl)-amide | X |
| 77 | (S)-4-Benzyl-1-[(S)-3-methyl-2-((S)-2-methylamino-propionylamino)-butyryl]-piperazine-2-carboxylic acid cycloheptylmethyl-amide | — |
| 78 | (S)-4-Benzyl-1-[(S)-3-methyl-2-((S)-2-methylamino-propionylamino)-butyryl]-piperazine-2-carboxylic acid indan-2-ylamide | X |
| 79 | (S)-4-Benzyl-1-[(S)-3-methyl-2-((S)-2-methylamino-propionylamino)-butyryl]-piperazine-2-carboxylic acid cyclohexylmethyl-amide | X |
| 80 | (S)-4-Benzyl-1-[(S)-3-methyl-2-((S)-2-methylamino-propionylamino)-butyryl]-piperazine-2-carboxylic acid (1-benzyl-2-phenyl-ethyl)-amide | X |
| 81 | (S)-4-Benzyl-1-[(S)-3-methyl-2-((S)-2-methylamino-propionylamino)-butyryl]-piperazine-2-carboxylic acid cyclopentylmethyl-amide | X |
| 82 | (S)-4-Benzyl-1-[(S)-3-methyl-2-((S)-2-methylamino-propionylamino)-butyryl]-piperazine-2-carboxylic acid (furan-2-ylmethyl)-amide | X |
| 83 | (S)-4-Benzyl-1-[(S)-3-methyl-2-((S)-2-methylamino-propionylamino)-butyryl]-piperazine-2-carboxylic acid (3-methyl-butyl)-amide | — |
| 84 | (S)-4-Benzyl-1-[(S)-3-methyl-2-((S)-2-methylamino-propionylamino)-butyryl]-piperazine-2-carboxylic acid 3,5-difluoro-benzylamide | X |
| 85 | (S)-N-{(S)-1-[(S)-4-Benzyl-2-(1,3-dihydro-isoindole-2-carbonyl)-piperazine-1-carbonyl]-2-methyl-propyl}-2-methylamino-propionamide | X |
| 86 | (S)-N-{(S)-1-[(S)-4-Benzyl-2-(3,4-dihydro-1H-isoquinoline-2-carbonyl)-piperazine-1-carbonyl]-2-methyl-propyl}-2-methylamino-propionamide | X |
| 87 | (S)-4-Benzyl-1-[(S)-3-methyl-2-((S)-2-methylamino-propionylamino)-butyryl]-piperazine-2-carboxylic acid ((R)-1-phenyl-ethyl)-amide | X |
| 88 | (S)-4-Benzyl-1-[(S)-3-methyl-2-((S)-2-methylamino-propionylamino)-butyryl]-piperazine-2-carboxylic acid (pyridin-3-ylmethyl)-amide | X, — |

"X" indicates an IC$_{50}$ value of less than 10 μM for XIAP.
"—" indicates an IC$_{50}$ value of equal or greater than 10 μM for XIAP.

EQUIVALENTS

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. The choice of starting material, synthesis method, or reaction conditions is believed to be a matter of routine for a person of ordinary skill in the art with knowledge of the embodiments described herein. Other aspects, advantages, and modifications considered to be within the scope of the following claims.

What is claim is:

1. Compounds of formula (I),

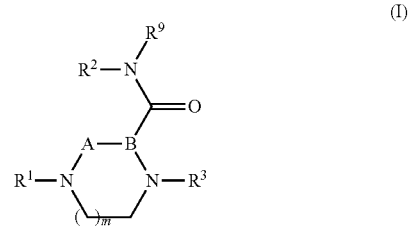

(I)

wherein

R$^1$ is a hydrogen atom, or an alkyl, heteroalkyl, alkenyl, heteroalkenyl, alkynyl, heteroalkynyl, aryl, heteroaryl, cycloalkyl, heterocycloalkyl, alkylcycloalkyl, heteroalkylcycloalkyl, aralkyl or heteroaralkyl radical, any of which may be further substituted with at least one halogen;

R$^2$ is an alkyl, heteroalkyl, alkenyl, heteroalkenyl, alkynyl, heteroalkynyl, aryl, heteroaryl, cycloalkyl, heterocycloalkyl, alkylcycloalkyl, heteroalkylcycloalkyl, aralkyl or heteroaralkyl radical, any of which may be further substituted with at least one halogen;

R$^3$ is chosen from one of the following structures:

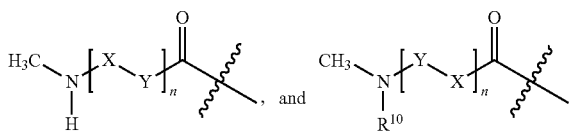

, and m is an integer 1, 2 or 3;

n is an integer 1, 2, 3, 4, 5 or 6;

A-B together are CHR$^4$—CH;

each X, independently of one another, is a bond, an oxygen atom, a sulfur atom, a group of formula CR$^6$R$^7$, CO, NR$^8$, an optionally substituted cycloalkylene, an optionally substituted heterocycloalkylene, an optionally substituted arylene, or an optionally substituted heteroarylene group;

each Y, independently of one another, is a bond, an oxygen atom, a sulfur atom, a group of formula CR$^6$R$^7$, CO, NR$^8$, an optionally substituted cycloalkylene, an optionally substituted heterocycloalkylene, an optionally substituted arylene, or an optionally substituted heteroarylene group;

R$^4$ is a hydrogen atom, a halogen atom, or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

the radicals R$^6$, independently of one another, are a hydrogen atom, or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

the radicals R$^7$, independently of one another, are a hydrogen atom, or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical; and the radicals R$^8$, independently of one another, are a hydrogen atom, or an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical;

R$^9$ is hydrogen or is an alkyl, heteroalkyl, aryl, heteroaryl, cycloalkyl, heterocycloalkyl, alkylcycloalkyl, heteroalkyl-cycloalkyl, aralkyl, or hetero-aralkyl radical, or R$^2$ and R$^9$ with the nitrogen atom may form a heteroaryl or heteroaralkyl; and R$^{10}$ is hydrogen or is an alkyl or heteroalkyl;

or a pharmacologically acceptable salt.

2. The compound according to claim 1, whereby R$^1$ is a C$_{1-10}$ alkyl group, —(CO)$_{0-1}$—(CH$_2$)$_{0-6}$—C$_{3-7}$-cycloalkyl, —(CO)$_{0-1}$—(CH$_2$)$_{0-6}$-phenyl, —(CO)$_{0-1}$—(CH$_2$)$_{0-6}$-naphthyl, (CO)$_{0-1}$—(CH$_2$)$_{0-6}$-heteroaryl or —(CO)$_{0-1}$—(CH$_2$)$_{0-6}$-heterocycloalkyl, whereby the cycloalkyl, phenyl, naphthyl, heteroaryl or heterocycloalkyl groups may optionally be substituted.

3. The compound according to claim 1 whereby R$^2$ is preferably C$_{1-10}$-alkyl, —(CH$_2$)$_{0-6}$—C$_{3-7}$-cycloalkyl, C$_{1-10}$alkyl-phenyl, C$_{1-10}$-alkyl-naphthyl, —(CH$_2$)$_{0-6}$—C$_{3-7}$-cycloalkyl-(CH$_2$)$_{0-6}$-phenyl-(CH$_2$)$_{0-4}$—CH((CH$_2$)$_{0-4}$-phenyl)$_2$, —(CH$_2$)$_{0-6}$-heterocycloalkyl or —(CH$_2$)$_{0-6}$-heteroaryl, whereby the cycloalkyl, phenyl, naphthyl, heteroaryl or heterocycloalkyl groups may optionally be substituted.

4. The compound according to claim 1 whereby R$^2$ is an optionally substituted benzyl, phenethyl or tetrahydronaphthyl group.

5. The compound according to claim 1, whereby R$^3$ is a group of formula CH$_3$—NH—CHR$^6$—CO—NH—CHR$^7$—CO—.

6. The compound according to claim 5, whereby the radicals R$^6$ and R$^7$, independently of one another, are C$_{1-10}$-alkyl, C$_{3-7}$-cycloalkyl or C$_{1-10}$ heteroalkyl groups.

7. The compound according to claim 5, whereby R$^6$ is a methyl group and R$^7$ is a group of formula —CH(CH$_3$)$_2$ or —C(CH$_3$)$_3$.

8. The compound according to claim 1, whereby m is an integer 1.

9. The compound according to claim 1, wherein A-B together are a group of formula CH$_2$—CH.

10. A pharmaceutical composition that comprises a pharmaceutically acceptable carrier and a therapeutically effective amount of a compound of formula I according to claim 1.

* * * * *